US010741034B2

(12) United States Patent
Berrada et al.

(10) Patent No.: US 10,741,034 B2
(45) Date of Patent: Aug. 11, 2020

(54) SECURITY SYSTEM AND METHOD OF MARKING AN INVENTORY ITEM AND/OR PERSON IN THE VICINITY

(71) Applicant: APDN (B.V.I.) Inc., Tortola (VG)

(72) Inventors: Abdelkrim Berrada, Lake Ronkonkoma, NY (US); MingHwa Benjamin Liang, East Setauket, NY (US); Lawrence Jung, Forest Hills, NY (US)

(73) Assignee: APDN (B.V.I.) INC., Tortola (VG)

( * ) Notice: Subject to any disclaimer, the term of this patent is extended or adjusted under 35 U.S.C. 154(b) by 269 days.

(21) Appl. No.: 14/570,242

(22) Filed: Dec. 15, 2014

(65) Prior Publication Data
US 2015/0302713 A1    Oct. 22, 2015

Related U.S. Application Data

(63) Continuation-in-part of application No. 13/652,781, filed on Oct. 16, 2012, now abandoned.

(51) Int. Cl.
| C12Q 1/68 | (2018.01) |
| G08B 15/02 | (2006.01) |
| C12Q 1/6876 | (2018.01) |
| B05D 1/00 | (2006.01) |

(52) U.S. Cl.
CPC ............ G08B 15/02 (2013.01); B05D 1/60 (2013.01); C12Q 1/68 (2013.01); C12Q 1/6876 (2013.01)

(58) Field of Classification Search
None
See application file for complete search history.

(56) References Cited

U.S. PATENT DOCUMENTS

| 4,183,989 A | 1/1980 | Tooth |
| 4,278,557 A | 7/1981 | Elwell, Jr. |
| 4,454,171 A | 6/1984 | Diggle, Jr. et al. |
| 4,548,955 A | 10/1985 | Okahata et al. |
| 4,683,195 A | 7/1987 | Mullis et al. |
| 4,739,044 A | 4/1988 | Stabinsky |
| 4,757,141 A | 7/1988 | Fung et al. |
| 4,849,208 A | 7/1989 | Stavrianopoulos |
| 4,861,620 A | 8/1989 | Azuma et al. |
| 4,965,188 A | 10/1990 | Mullis et al. |
| 5,047,519 A | 9/1991 | Hobbs, Jr. et al. |
| 5,075,216 A | 12/1991 | Innis et al. |
| 5,089,691 A | 2/1992 | Morisaki et al. |
| 5,132,242 A | 7/1992 | Cheung |
| 5,139,812 A | 8/1992 | Lebacq |
| 5,151,507 A | 9/1992 | Hobbs, Jr. et al. |
| 5,156,765 A | 10/1992 | Smrt et al. |
| 5,176,203 A | 1/1993 | Larzul |
| 5,270,183 A | 12/1993 | Corbett et al. |
| 5,415,839 A | 5/1995 | Zaun et al. |
| 5,429,952 A | 7/1995 | Garner et al. |
| 5,451,505 A | 9/1995 | Dollinger |
| 5,498,283 A | 3/1996 | Botros et al. |
| 5,508,197 A | 4/1996 | Hansen et al. |
| 5,595,871 A | 1/1997 | DelVecchio et al. |
| 5,599,578 A | 2/1997 | Butland |
| 5,602,381 A | 2/1997 | Hoshino et al. |
| 5,639,603 A | 6/1997 | Dower et al. |
| 5,643,728 A | 7/1997 | Slater et al. |
| 5,736,314 A | 4/1998 | Hayes et al. |
| 5,763,176 A | 6/1998 | Slater et al. |
| 5,776,713 A | 7/1998 | Garner et al. |

(Continued)

FOREIGN PATENT DOCUMENTS

| CN | 1508696 | 6/2004 |
| EP | 0 477 220 B1 | 4/1992 |

(Continued)

OTHER PUBLICATIONS

S. Hou, X. Li and X-Z Feng Method to improve DNA Condesation Efficiency by Alkali Treatment. Nucleosides, Nucleotides and Nucleic Acids, 2009. 28:725-735.Taylor & Francis Group, LLC.
M. Ageno, E. Dore and C. Frontali The Alkaline Denaturation of DNA, Biophys. J. Nov. 1969, 9(11): 1281. Abstract.
M. Ageno, E. Dore and C. Frontali The Alkaline Denaturation of DNA, Biophys. J. Nov. 1969, 9(11): 1281-1311.
T. Thiel, L. Liczkowski and S.T. Bissen New zwitterionic butanesulfonic acids that extend the alkaline range of four families of good buffers: Evaluation for use in biological Systems. J. Biochem. Biophys. Methods (1998) 37: 117-129. Elsevier.
Versalift, "Market Growth, the evolution of the aerial lift industry," Oct. 1, 2002. Accessed on web Nov. 10, 2008.

(Continued)

Primary Examiner — Robert T. Crow
(74) Attorney, Agent, or Firm — Clay D. Shorrock

(57) ABSTRACT

A method of marking an inventory item includes providing an activatable smoke generator and a reservoir for holding a smoke fluid and adapted to provide a flow of smoke fluid to the generator. The reservoir contains a smoke fluid including a carrier nucleic acid having a uniquely identifiable sequence, and upon activation of the smoke generator, marker smoke is generated and targeted to flow over the inventory item. The method further includes activating the smoke generator to produce the marker smoke including the carrier nucleic acid so as to cause the marker smoke to flow over the inventory item and thereby to detectably mark the inventory item with carrier nucleic acid. The invention provides methods for stably binding and immobilizing deoxyribonucleic acid onto objects and substrates. The method includes exposing the deoxyribonucleic acid to alkaline conditions, and contacting the deoxyribonucleic acid to the object or substrate. The alkaline conditions are produced by mixing the deoxyribonucleic acid with an alkaline solution having a pH of about 9.0 or higher, and contacting the deoxyribonucleic acid to the substrate. The immobilized DNA can be used as a taggant and can be used in combination with other detectable taggants, such as optical reporters.

8 Claims, 5 Drawing Sheets

(56) References Cited

U.S. PATENT DOCUMENTS

| | | | |
|---|---|---|---|
| 5,866,336 A | 2/1999 | Nazarenko et al. | |
| 5,912,257 A | 6/1999 | Prasad et al. | |
| 5,942,444 A | 8/1999 | Rittenburg et al. | |
| 5,956,172 A | 9/1999 | Downing et al. | |
| 5,977,436 A | 11/1999 | Thomas et al. | |
| 5,989,823 A | 11/1999 | Jayasena et al. | |
| 6,013,789 A | 1/2000 | Rampal | |
| 6,030,657 A | 2/2000 | Butland et al. | |
| 6,033,880 A | 3/2000 | Haff et al. | |
| 6,057,370 A | 5/2000 | Weiland et al. | |
| 6,127,120 A | 10/2000 | Graham et al. | |
| 6,132,996 A | 10/2000 | Hunicke-Smith | |
| 6,140,075 A | 10/2000 | Russell et al. | |
| 6,169,174 B1 | 1/2001 | Hasegawa et al. | |
| 6,261,809 B1 | 7/2001 | Bertling et al. | |
| 6,287,768 B1 | 9/2001 | Chenchik et al. | |
| 6,312,911 B1 | 11/2001 | Bancroft et al. | |
| 6,326,489 B1 | 12/2001 | Church et al. | |
| 6,342,359 B1 | 1/2002 | Lee et al. | |
| 6,361,944 B1 | 3/2002 | Mirkin et al. | |
| 6,379,897 B1 | 4/2002 | Weidenhammer et al. | |
| 6,399,397 B1 | 6/2002 | Zarling et al. | |
| 6,537,747 B1 | 3/2003 | Mills, Jr. et al. | |
| 6,537,752 B1 | 3/2003 | Astle | |
| 6,576,422 B1 | 6/2003 | Weinstein et al. | |
| 6,608,228 B1 | 8/2003 | Cumpston et al. | |
| 6,613,560 B1 | 9/2003 | Tso et al. | |
| 6,632,653 B1 | 10/2003 | Astle | |
| 6,686,149 B1 | 2/2004 | Sanchis et al. | |
| 6,703,228 B1 | 3/2004 | Landers | |
| 6,709,692 B2 | 3/2004 | Sudor | |
| 6,743,640 B2 | 6/2004 | Whitten et al. | |
| 6,995,256 B1 | 2/2006 | Li et al. | |
| 7,014,113 B1 | 3/2006 | Powell et al. | |
| 7,015,030 B1 | 3/2006 | Fouillet et al. | |
| 7,031,927 B1 | 4/2006 | Beck et al. | |
| 7,060,874 B2 | 6/2006 | Wilkins | |
| 7,112,616 B2 | 8/2006 | Takizawa et al. | |
| 7,115,301 B2 | 10/2006 | Sheu et al. | |
| 7,133,726 B1 | 11/2006 | Atwood et al. | |
| 7,160,996 B1 | 1/2007 | Cook | |
| 7,223,906 B2 | 5/2007 | Davis | |
| 7,250,195 B1 | 7/2007 | Storey et al. | |
| 7,709,250 B2 | 5/2010 | Corbett et al. | |
| 7,732,492 B2 | 6/2010 | Makino et al. | |
| 2,428,925 A1 | 3/2012 | Schmitz | |
| 8,278,807 B2 | 10/2012 | Agneray et al. | |
| 8,597,549 B2 | 12/2013 | Cumpston et al. | |
| 9,266,370 B2 | 2/2016 | Jung et al. | |
| 9,297,032 B2 | 3/2016 | Jung | |
| 2001/0039018 A1 | 11/2001 | Matson et al. | |
| 2002/0048822 A1 | 4/2002 | Rittenburg et al. | |
| 2002/0051969 A1 | 5/2002 | Goto et al. | |
| 2002/0056147 A1 | 5/2002 | Dau et al. | |
| 2002/0064639 A1 | 5/2002 | Rearick | |
| 2002/0080994 A1 | 6/2002 | Lofgren et al. | |
| 2002/0119485 A1 | 8/2002 | Morgan | |
| 2002/0128234 A1 | 9/2002 | Hubbell et al. | |
| 2002/0137893 A1 | 9/2002 | Burton et al. | |
| 2002/0155490 A1 | 10/2002 | Skinner et al. | |
| 2002/0160360 A1 | 10/2002 | Chenchik et al. | |
| 2002/0167161 A1 | 11/2002 | Butland | |
| 2002/0129251 A1 | 12/2002 | Itakura | |
| 2002/0187263 A1 | 12/2002 | Sheu et al. | |
| 2003/0000225 A1 | 1/2003 | Nagai et al. | |
| 2003/0017551 A1 | 1/2003 | Parthasarathy et al. | |
| 2003/0035917 A1 | 2/2003 | Hyman | |
| 2003/0064507 A1 | 4/2003 | Gallagher et al. | |
| 2003/0096273 A1 | 5/2003 | Gagna | |
| 2003/0142704 A1 | 7/2003 | Lawandy | |
| 2003/0142713 A1 | 7/2003 | Lawandy | |
| 2003/0162296 A1 | 8/2003 | Lawandy | |
| 2003/0177095 A1 | 9/2003 | Zorab et al. | |
| 2003/0203387 A1 | 10/2003 | Pelletier | |
| 2003/0207331 A1 | 11/2003 | Wilson, Jr. et al. | |
| 2004/0050701 A1 * | 3/2004 | McEntee | C12M 25/08 204/465 |
| 2004/0063117 A1 | 4/2004 | Rancien et al. | |
| 2004/0071718 A1 | 4/2004 | Tsai | |
| 2004/0115796 A1 | 6/2004 | Burns | |
| 2004/0166520 A1 | 8/2004 | Connolly | |
| 2004/0219287 A1 | 11/2004 | Regan et al. | |
| 2005/0008762 A1 | 1/2005 | Sheu et al. | |
| 2005/0031120 A1 | 2/2005 | Samid | |
| 2005/0053968 A1 | 3/2005 | Bharadwaj et al. | |
| 2005/0059029 A1 | 3/2005 | Raymond et al. | |
| 2005/0059059 A1 | 3/2005 | Liang | |
| 2005/0089970 A1 * | 4/2005 | Bradburne | C07K 14/7158 435/69.5 |
| 2005/0112610 A1 | 5/2005 | Lee | |
| 2005/0142565 A1 | 6/2005 | Samper et al. | |
| 2005/0214532 A1 | 9/2005 | Kosak et al. | |
| 2005/0260609 A1 | 11/2005 | Lapidus | |
| 2006/0017957 A1 | 1/2006 | Degott et al. | |
| 2006/0017959 A1 | 1/2006 | Downer et al. | |
| 2006/0117465 A1 | 6/2006 | Willows et al. | |
| 2006/0121181 A1 | 6/2006 | Sleat et al. | |
| 2006/0199196 A1 | 9/2006 | O'Banion et al. | |
| 2006/0286569 A1 | 12/2006 | Bar-Or et al. | |
| 2007/0012784 A1 | 1/2007 | Mercolino | |
| 2007/0026239 A1 | 2/2007 | Sigrist et al. | |
| 2007/0048761 A1 | 3/2007 | Reep et al. | |
| 2007/0072197 A1 | 3/2007 | Rayms-Keller et al. | |
| 2007/0117119 A1 | 5/2007 | Akita et al. | |
| 2007/0121937 A1 | 5/2007 | Kochevar et al. | |
| 2007/0254292 A1 | 11/2007 | Fukasawa | |
| 2008/0045288 A1 | 2/2008 | Chen | |
| 2008/0081357 A1 | 4/2008 | Kwon et al. | |
| 2008/0149713 A1 | 6/2008 | Brundage | |
| 2008/0153135 A1 | 6/2008 | Liu | |
| 2008/0216255 A1 | 9/2008 | Poovey et al. | |
| 2008/0293052 A1 | 11/2008 | Liang et al. | |
| 2008/0299559 A1 | 12/2008 | Kowk et al. | |
| 2009/0042191 A1 | 2/2009 | Hayward et al. | |
| 2009/0057147 A1 | 3/2009 | Kayyem | |
| 2009/0075261 A1 | 3/2009 | Hayward et al. | |
| 2009/0136163 A1 | 5/2009 | Kerr et al. | |
| 2009/0220789 A1 | 9/2009 | DeSimone et al. | |
| 2009/0222912 A1 | 9/2009 | Boschin | |
| 2009/0253127 A1 | 10/2009 | Gaudreau et al. | |
| 2009/0286250 A1 | 11/2009 | Hayward et al. | |
| 2009/0069199 A1 | 12/2009 | Brandenburg | |
| 2009/0311555 A1 | 12/2009 | Badyal et al. | |
| 2009/0313740 A1 | 12/2009 | Santos et al. | |
| 2010/0050344 A1 | 3/2010 | Peltz et al. | |
| 2010/0075407 A1 | 3/2010 | Duffy et al. | |
| 2010/0099080 A1 | 4/2010 | Church et al. | |
| 2010/0149531 A1 | 6/2010 | Tang | |
| 2010/0240101 A1 | 9/2010 | Lieberman et al. | |
| 2010/0250616 A1 | 9/2010 | Kim | |
| 2010/0258743 A1 | 10/2010 | Bortolin | |
| 2010/0285447 A1 | 11/2010 | Walsh et al. | |
| 2010/0285490 A1 | 11/2010 | Dees et al. | |
| 2010/0285985 A1 | 11/2010 | Liang et al. | |
| 2010/0307120 A1 | 12/2010 | Stover | |
| 2011/0014133 A1 * | 1/2011 | Grunstein | C12N 15/1138 424/43 |
| 2011/0054938 A1 | 3/2011 | Hood et al. | |
| 2011/0165569 A1 | 7/2011 | Macula | |
| 2011/0229881 A1 | 9/2011 | Oshima | |
| 2011/0250594 A1 | 10/2011 | Liang et al. | |
| 2011/0263688 A1 | 10/2011 | Barany et al. | |
| 2012/0115154 A1 | 5/2012 | Hampikian | |
| 2012/0264742 A1 | 10/2012 | Furuishi | |
| 2013/0040150 A1 | 2/2013 | Trexler et al. | |
| 2013/0046994 A1 | 2/2013 | Shaw | |
| 2013/0048731 A1 | 2/2013 | Flickner et al. | |
| 2013/0109596 A1 | 5/2013 | Peterson et al. | |
| 2013/0234043 A1 | 9/2013 | Hussain et al. | |
| 2013/0274129 A1 | 10/2013 | Katzen et al. | |
| 2014/0099643 A1 | 4/2014 | Jung et al. | |
| 2014/0106357 A1 | 4/2014 | Berrada et al. | |
| 2014/0224673 A1 | 8/2014 | Alocija | |
| 2014/0256881 A1 | 9/2014 | Berrada et al. | |

(56) References Cited

U.S. PATENT DOCUMENTS

| | | |
|---|---|---|
| 2014/0272097 A1 | 9/2014 | Jung et al. |
| 2015/0018538 A1 | 1/2015 | Berrada et al. |
| 2015/0030545 A1 | 1/2015 | Grass et al. |
| 2015/0083797 A1 | 3/2015 | Tran et al. |
| 2015/0133319 A1 | 3/2015 | Fu et al. |
| 2015/0107475 A1 | 4/2015 | Jung et al. |
| 2015/0125949 A1 | 5/2015 | Liss |
| 2016/0168781 A1 | 6/2016 | Tran et al. |
| 2016/0326511 A1 | 11/2016 | Berrada et al. |

FOREIGN PATENT DOCUMENTS

| | | |
|---|---|---|
| EP | 0 623 658 A2 | 11/1994 |
| EP | 0840350 A2 | 5/1998 |
| EP | 1063286 | 12/2000 |
| EP | 1231470 | 8/2002 |
| EP | 1237327 | 9/2002 |
| EP | 140333 A1 | 3/2004 |
| EP | 1847316 | 10/2007 |
| EP | 2428925 | 3/2012 |
| EP | 2444136 | 4/2012 |
| EP | 2444136 A | 4/2012 |
| EP | 2444546 | 4/2012 |
| GB | 2319337 | 6/1998 |
| GB | 2434570 A1 | 8/2007 |
| JP | 63503242 | 11/1988 |
| JP | 06187239 | 7/1994 |
| JP | 2000250812 | 9/2000 |
| JP | 2001034533 | 2/2001 |
| JP | 2009517250 | 4/2009 |
| RU | 2084535 C | 7/1997 |
| RU | 2170084 C1 | 7/2001 |
| WO | 8706383 A1 | 10/1987 |
| WO | 90/144441 A1 | 11/1990 |
| WO | WO9204469 | 3/1992 |
| WO | 9506249 A1 | 3/1994 |
| WO | 9502702 A1 | 1/1995 |
| WO | 9806084 A1 | 2/1996 |
| WO | WO9704392 | 2/1997 |
| WO | 9745539 A1 | 12/1997 |
| WO | WO9816313 | 4/1998 |
| WO | WO9945514 | 9/1999 |
| WO | 9959011 A1 | 11/1999 |
| WO | WO0061799 | 10/2000 |
| WO | 0125002 A1 | 4/2001 |
| WO | 0136676 A | 5/2001 |
| WO | 2001036676 | 5/2001 |
| WO | 0055609 A1 | 9/2001 |
| WO | 0199063 A1 | 12/2001 |
| WO | 02057548 A1 | 7/2002 |
| WO | 02084617 A1 | 10/2002 |
| WO | WO03016558 | 2/2003 |
| WO | 03030129 A2 | 4/2003 |
| WO | WO03038000 | 5/2003 |
| WO | 30/080931 A1 | 10/2003 |
| WO | 2004025562 A1 | 3/2004 |
| WO | WO2004086323 | 7/2004 |
| WO | WO2005103226 | 11/2005 |
| WO | WO2006109014 | 10/2006 |
| WO | 2007078833 A | 7/2007 |
| WO | WO2008007060 | 1/2008 |
| WO | 2008154931 A | 12/2008 |
| WO | 100075858 A1 | 3/2010 |
| WO | WO2012076021 | 6/2012 |
| WO | WO2013052924 | 4/2013 |
| WO | WO2013154943 | 10/2013 |
| WO | 2013170009 A1 | 11/2013 |
| WO | WO2014062754 | 4/2014 |

OTHER PUBLICATIONS

Schulz et al., "Archived or directly swabbed latent fingerprints as a DNA source for STR typing," Forensic Science International, 127 (2002) 128-130.

Zuckermann, et al. "Efficient methods for attachment of thiol specific probes to the 3' end of synthetic oligonucleotides." Nucleic Acids Research, vol. 15, pp. 5305-5321 (1987) IRL Press Limited, Oxford.

Whitcombe, et al. "Detection of PCR products using self-probing amplicons and fluorescence," Nature Biotechnology, vol. 17 pp. 804-807 (1999) Nature America, Inc. New York.

Tyagi, et al. Multicolor molecular beacons for allele discrimination, Nature Biotechnology, vol. 16, pp. 49-53 (1998) Nature Publishing Group, New York.

Nazarenko, et al. "A closed tube format for amplification and detection of DNA based on energy transfer," Nucleic Acids Research, vol. 25, pp. 2516-2521 (1997) Oxford University Press.

Tyagi & Kramer, "Molecular Beacons: Probes that Fluoresce upon Hybridization" nature Biotechnology, vol. 14, pp. 303-308 (1996) Nature Publishing Group, New York.

Sproat, et al. "The synthesis of protected 5'-mercapto-2',5'-didoexyribonucleoside-3-O-phosphoramidites, uses of 5'-mercapto-didoexyribonucleosides." Nucleic Acids Research, vol. 15, pp. 4837-4848 (1987) IRL Press Limited, Oxford.

Nelson, "Bifunctional oligonucleotide probes synthesized using a novel CPG support are able to detect single base pair mutations." Nucleic Acids Research, vol. 17, pp. 7187-7194 (1989) IRL Press Limited, Oxford.

Gupta, et al. "A general method for the synthesis of 3'-sulfhydryl and phosphate group containing oligonucleotides." Nucleic Acids Research, vol. 19, pp. 3019-3025 (1991) Oxford University Press, Oxford, England.

Lee, et al. "Allelic discrimination by nick translation PCR with fluorescent probes." Nucleic Acids Research, vol. 21, pp. 3761-3766 (1993) Oxford University Press, Oxford, England.

Holland, et al. "Detection of specific polymerase chain reaction product by utilizing the 5' [to] 3' exonuclease activity of Thermus aquaticus DNA polymerase." Proceedings of the National Academy of Sciences, USA vol. 86 pp. 7276-7280 (1991) National Academy of Sciences, Washington, DC.

Reid, et al. "Real Time Quantitative PCR." Genome Research, vol. 6, pp. 986-994 (1996) Cold Spring Harbor Laboratory Press, Woodbury, New York.

Gibson, et al. "A Novel Method for Real Time Quantitative RT-PCR" Genome Research, vol. 6, pp. 995-1001 (1996) Cold Spring Harbor Laboratory Press, Woodbury, New York.

Agrawal & Tang, "Site-specific functionalization of oligodoexynucleotides for non-radioactive labelling." Tetrahedron Letters, vol. 31, pp. 1543-1546 (1990) Pergamon Press, Great Britain.

Van Der Rijke, et al. "Up-converting phosphor reporters for nucleic acid microarrays." Nature Biotechnology, vol. 19, pp. 273-276 (2001) Nature Publishing Group, New York.

Corstjens, et al. "Infrared Up-converting phosphors for bioassays." IEE Proceedings-Nanobiotechnology, vol. 152, pp. 64-72 (2005) Institution of Engineering and Technology, London.

Hussein et al. "Molecular Characterization of Cotton Genotypes Using PCR-based Markers." Journal of Applied Sciences Research 3(10) 1156-1169 (2007). INSInet Publication.

Jiang, et al. "Polyploid formatioopn created unique avenues for response to selection in *Gossypium* (cotton)" Proceedings of the National Academy of Sciences, USA vol. 95 pp. 4419-4424 (1998) National Academy of Sciences, Washington, DC.

Lee, et al. "The complete genome sequence of Gossypium hursutum, organization and phylogenetic relationships to ether angiosperms." BMC Genomics 7:61, Mar. 2006.

Ibrahim, et al. Complete nucleotide sequence of the cotton (*Gossypium barbadense* L.) chloroplast genome with a comparative analysis of sequence among 9 dicot plants. Genes and Genetic Systems vol. 81. pp. 311-321 (2006).

Kaneda, S. et al. Modification of the glass surface property in PDMS-glass hybrid microfluidoc devces. Analytical Sciences, Jan. 2012, vol. 28, No. 1, pp. 39-44.

Hosokawa, K. et al. DNA Detection on a power-free microchip with laminar flow-assisted dendritic amplification. Analytical Sciences, 2010, Vo. 26, No. 10, pp. 1052-1057.

(56) References Cited

OTHER PUBLICATIONS

Park, H. et al. Stress response of fibroblasts adherent to the surface of plasma-treated poly(lactic-co-glucolic acid) nanofiber matrices. Colloids surf B Biointerfaces, May 2010, 1; 77(1):90-95.

Tuzlakoglu K. et al. A new route to produce starch-based fiber mesh scaffolds by wet spinning and subsequent surface modification as a way to improve cell attachment and proliferation. J Biomed Mater Res A, Jan. 2010, 92(1):369-377.

Karahan et al., Fibers and Polymers, vol. 9, pp. 21-26 (2008).

Ullrich, T. et al. Competitive reporter monitored amplification (CMA)-quantification of molecular targets by real time monitoring of competitive reporter hybridization. PLoS One, 2012, vol. 7, No. 4 E35438. doi;I0.1371/journal.pone.0035438, p. 1-13.

Beija, Mariana; et al. Synthesis and applications of Rhodamine derivatives as fluorescent probes (2009) Critical Reviews, vol. 38: pp. 2410-2433. Chemical Society Reviews; Advance article published on the web Apr. 27, 2009.

Yang, X.F. et al. Fluorometric determination of hemoglobin using spiro form rhodamine B hydrazide in a micellar medium, Tantala, vol. 62(4):439-445; Nov. 12, 2003.

Instant Krazy Glue, product description, accessed website Feb. 24, 2012, 4 pages.

"Virus" (Wikipedia.com, accessed Nov. 24, 2012).

"How many species of bacteria are there" (wisegeek.com; accessed Jan. 21, 2014).

"Fungi" (Wikipedia.com; accessed Jun. 3, 2013).

"List of sequenced bacterial genomes" (Wikipedia.com; accessed Jan. 24, 2014).

"Fish" (Wikipedia.com; accessed Nov. 2, 2014).

"Mammal" (Wikipedia.com; accessed Sep. 22, 2011).

"Murinae" (Wikipedia.com; accessed Sep. 22, 2011).

"Plant" (Wikipedia.com; accessed Mar. 8, 2013).

International Preliminary Report on Patentability for Application No. PCT/US2013/065161 dated Apr. 21, 2015.

Hashimoto, Masahiko et al., "Rapid PCR in a Continuous Flow Device", Lab Chip, 4, 638-645 (2004).

Written Opinion of the International Search Authority for PCT/US15/21165 dated Jul. 2, 2015.

Written Opinion of the International Search Authority for PCT/US2015/013084 dated Apr. 17, 2015.

Chrisey et al., "Fabrication of Patterned DNA Surfaces," Nucleic Acids Research, Information Retrieval Ltd, GB, vol. 24, No. 15, Jan. 1, 1996, pp. 3040-3047, XP002913337.

Khandjian, "Optimized Hybridization of DNA Blotted and Fixed to Nitrocellulose and Nylon Membranes," Bio-Technology (New York), vol. 5, No. 2, 1987, pp. 165-167, XP002762699.

Aleksandr Ovsianikov et al., "Two-photon Polymerization Technique for Microfabrication of CAD-designed 3D Scaffolds from Commercially Available Photosensitive Materials," Journal of Tissue Engineering and Regenerative Medicine, vol. 1, No. 6, Nov. 10, 2007, pp. 443-449, XP055308966.

Jim Hayward et al., "A Scaled, Integrative Implementation for DNA Marking of Integrated Circuits," Apr. 18, 2013, XP055308145, URL: http://www.erai.com/CustomUploads/conference/2013/PDF/APDNAApril18.pdf.

F. Fixe et al., "Thin Film Micro Arrays with Immobilized DNA for Hybridization Analysis," MRS Online Proceedings, vol. 723, Jan. 1, 2002, XP055308987.

Skirtach et al., "The Role of Metal Nanoparticles in Remote Release of Encapsulated Materials," Nano Letters, vol. 5, No. 7, 2005, pp. 1371-1377.

Supplementary European Search Report for Corresponding European Application No. EP14820538, pp. 1-8.

Kim et al., "Fabrication and characterization of a PDMS-glass hybrid continuous-flow PCR chip," Biochemical Engineering Journal, 2006, vol. 29, pp. 91-97.

Kopp et al., "Chemical Amplification: Continuous-Flow PCR on a Chip," Science, vol. 280, May 15, 1998, pp. 1046-1048.

Curcio et al., "Continuous Segmented-Flow Polymerase Chain Reaction for High-Throughput Miniaturized DNA Amplification," Analytical Chemistry, vol. 75, No. 1, Jan. 1, 2003, pp. 1-7.

Obeid, Pierre J. et al., "Microfabricated Device for DNA and RNA Amplification by Continuous-Flow Polymerase Chain Reaction and Reverse Transcription-Polymerase Chain Reaction with Cycle Number Section", Anal. Chem, 75, 288-295 (2003).

Berger et al., "Flow in Curved Pipes," Ann. Rev. Fluid Mech, v. 15, 1983, pp. 461-512.

Takara Bio, "Takara Bio to Produce DNA Fragments for DNA Microarrays on Industrial Scale", http://www.evaluategroup.com/Universal/View.aspx?type_Story&id.

* cited by examiner

SECURITY SYSTEM AND METHOD OF MARKING AN INVENTORY ITEM AND/OR PERSON IN THE VICINITY

RELATED APPLICATIONS

This application is a continuation-in-part of U.S. patent application Ser. No. 13/652,781 filed Oct. 16, 2012, which is incorporated herein by reference in its entirety.

TECHNICAL FIELD

The present invention relates to a security system and methods of marking an inventory item and/or a person in the vicinity of the inventory item. More particularly, the present invention relates to incorporating a carrier nucleic acid that includes a DNA taggant having a unique identifiable sequence into a smoke fluid, and discharging the smoke fluid including the carrier nucleic and the DNA taggant onto various surfaces for inventory identification, authentication or tracking, as well as for marking intruders.

BACKGROUND

The retail industry is often faced with a dilemma. On the one hand, how to make their displays open and inviting to potential purchasers, while on the other hand still protecting their inventory and most valuable items from theft.

Robberies from retailers or other businesses usually happen very quickly and often involve high value items. The perpetrators attempting this type of theft act very quickly and may use threats or violence to intimidate staff and to circumvent traditional security systems. Moreover, conventional security measures such as silent alarms and surveillance cameras are routinely ignored by determined criminals and thus these security measures are typically ineffective in preventing breaking and entering premises such as homes and businesses, and subsequent theft of valuables or inventory.

In order to address the above-mentioned issues, security systems including smoke generators or fog generators have been developed. These systems can in just a few seconds produce a thick cloud of artificial disorienting and impenetrable smoke or fog. In contrast to surveillance cameras and alarms, smoke or fog security systems immediately stop intruders and would be thieves in their tracks by obscuring everything from sight within seconds. This disorienting fog usually results in redirecting the intruders' efforts from targeting valuables for theft to finding an exit from the building.

The security smoke or fog systems can also be used in conjunction with audio and lighting to provide an even stronger deterrent. These systems are designed to provide protection in that critical time between activation of the system and the arrival of a response team.

The dense disorienting smoke or fog causes would be thieves to lose the ability to strike quickly, as they are distracted by the intense fog which also prevents them from being able to distinguish the most valuable items they were attempting to steal. When such a dense smoke or fog is activated most intruders will immediately abandon any attempt to make off with valuables and seek to leave the area as quickly as possible.

Security smoke or fog generators can be easily integrated into existing alarm systems, such as access and control systems and closed circuit television (CCTV) security systems. However, while these security smoke or fog systems may prevent theft and/or minimize the amount of such theft, the available security smoke or fog systems do not provide a method to later identify the intruders/thieves and/or uniquely identify any recovered inventory item that were missing from the premises.

Thus, there is still a need in the art for a security smoke or fog system which not only deters intruders and theft, but also provides a proven reliable method of identifying whether a person of interest was present when the smoke or fog system was activated, and uniquely identifies inventory items marked by the activated smoke or fog system.

SUMMARY

In accordance with an exemplary embodiment of the present invention, a method of marking an inventory item is provided. The method includes providing an activatable smoke generator and a reservoir for holding a smoke fluid and adapted to provide a flow of smoke fluid to the generator. The reservoir contains a smoke fluid incorporating a carrier nucleic acid that includes a DNA taggant having a uniquely identifiable sequence. The method further includes activating the smoke generator to produce the marker smoke including the carrier nucleic acid that includes the DNA taggant so as to cause the marker smoke to flow over the inventory item and thereby to detectably mark the inventory item with the carrier nucleic acid and DNA taggant.

In another embodiment the present invention also provides a method of marking a person in the vicinity of an activated smoke generator, the method includes providing an activatable smoke generator and a reservoir for holding a marker smoke fluid and adapted to provide the flow of marker smoke fluid to the generator; the reservoir containing a marker smoke fluid incorporating a carrier nucleic acid that includes a DNA taggant having a uniquely identifiable sequence, and activating the smoke generator to produce the marker smoke including the carrier nucleic acid and the DNA taggant so as to cause the marker smoke to flow over a person in the vicinity of the smoke generator and thereby to detectably mark the exposed body surface and/or one or more items of clothing of the person with the carrier nucleic acid and the DNA taggant.

In still another exemplary embodiment, a security system is provided. The security system includes an activatable smoke generator, a reservoir for holding a smoke fluid and adapted to provide a flow of smoke fluid to the generator, wherein the smoke fluid includes a carrier nucleic acid that includes a DNA taggant having a uniquely identifiable sequence.

The present invention provides methods of immobilizing a deoxyribonucleic acid to a substrate or of binding a deoxyribonucleic acid to a substrate. The method includes exposing the deoxyribonucleic acid to alkaline pH, and contacting the alkaline exposed deoxyribonucleic acid to the substrate.

One embodiment of the present invention provides a method of binding of a deoxyribonucleic acid to a substrate, wherein the method includes exposing the deoxyribonucleic acid to alkaline conditions wherein the alkaline conditions are produced by mixing the deoxyribonucleic acid with an alkaline solution having a high pH (such as for instance a pH of about 9.0 to about 14.0), and contacting the alkaline-exposed deoxyribonucleic acid to the substrate. In one embodiment, the alkaline solution is a solution of a hydroxide of an alkali metal.

In another embodiment of the present invention, the alkaline solution is a solution of a high pH buffer. In another embodiment, the high pH buffer is selected from the group consisting of CABS (4-[cyclohexylamino]-1-butanesulphonic acid), CAPS (N-cyclohexyl-3-amino-propanesulfonic acid), AMP (2-amino-2-methyl-1-propanol), CAPSO (N-cyclohexyl-2-hydroxyl-3-aminopropanesulfonic acid), CHES (2-(N cyclohexylamino) ethanesulphonic acid), AMPSO (3-[(1,1-dimethyl-2-hydroxyethyl) amino]-2-hydroxypropanesulfonic acid) and a mixture of any two or more of the foregoing.

BRIEF DESCRIPTION OF THE DRAWINGS

Examplary embodiments of the inventive concept can be more clearly understood from the following detailed description taken in conjunction with the accompanying figures.

DETAILED DESCRIPTION

Figure 1:
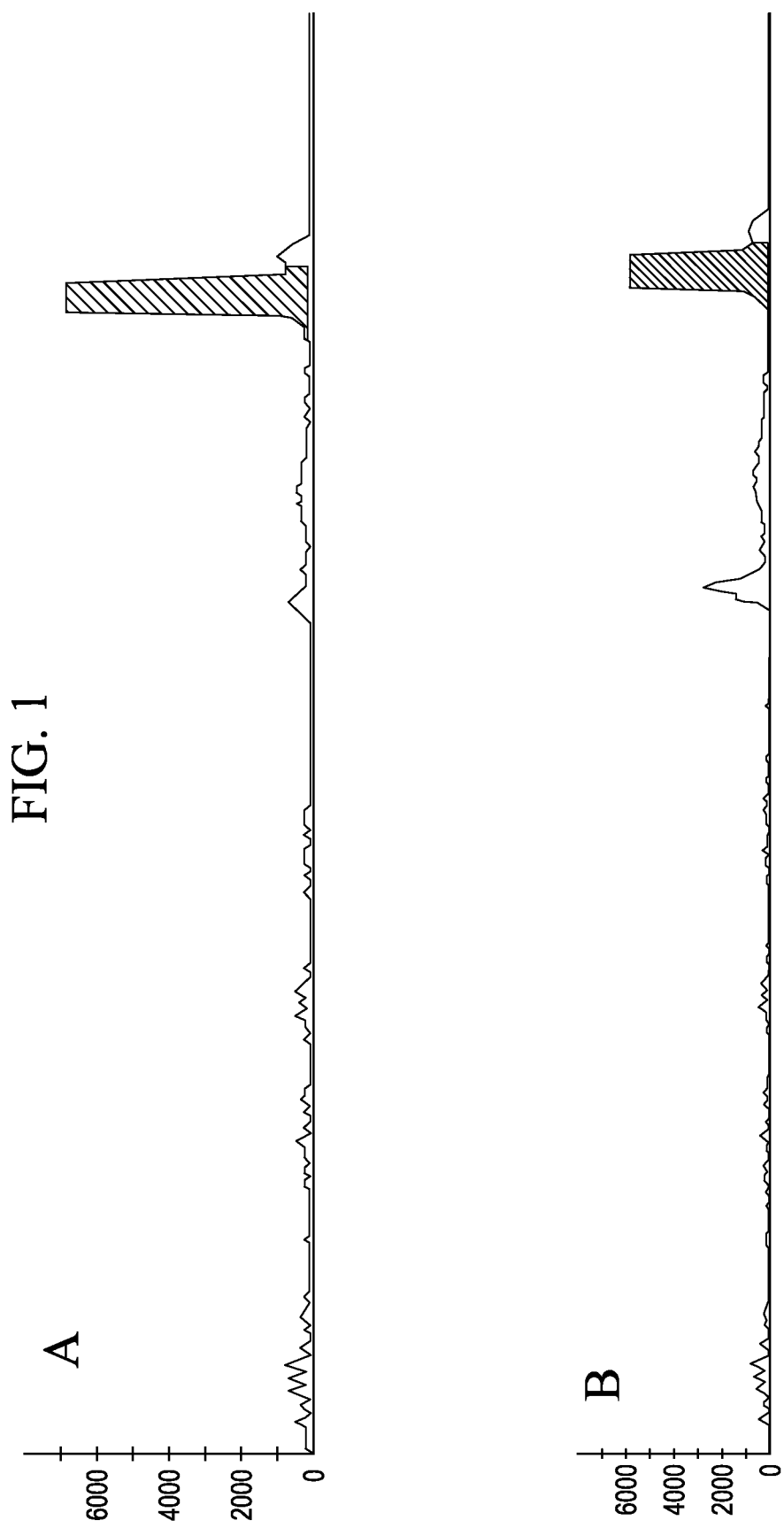
FIG. 1 shows data representative of DNA amplification and detection from cotton and wool textile fabrics after exposure to a marker smoke that contains a carrier nucleic acid that includes a DNA taggant having a uniquely identifiable sequence. Panel A is a trace from a capillary electrophoresis separation of PCR amplification products from a sample of cotton fabric exposed to marker smoke containing the DNA taggant having a uniquely identifiable sequence. Panel B is a similar trace from a different PCR amplification from a sample of wool fabric exposed to marker smoke containing the DNA taggant having a uniquely identifiable sequence.

Definitions:
Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "DNA taggant" means a nucleic acid tag which comprises deoxy nucleotides. A DNA taggant may be double stranded or single stranded, cDNA, STR (short tandem repeats) and the like. The DNA taggant may also include modification to one or more nucleotides which aid in the identification or detection of the DNA taggant. The term "DNA taggant" as used herein means a DNA maker comprising a uniquely identifiable sequence that can be utilized to identify or authenticate a particular item or product, or even to identify or authenticate the exposed body surface or hair of a person exposed to marker smoke or fog containing the DNA taggant.

The term "identifiable sequence" or "detectable sequence" means a nucleotide sequence which can be detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

The term "inventory item" as used herein is defined as any inanimate object within the range of the marker smoke or fog produced from a smoke generator.

The term "linker" means a compound or a composition which covalently links a biomolecule to the surface of a coated emitting reporter. For example, but not limited to a silylated coated upconverting phosphor particle linked to a DNA molecule.

The term "monomer" as used herein refers to any chemical entity that can be covalently linked to one or more other such entities to form an oligomer or a polymer. Examples of "monomers" include nucleotides, amino acids, saccharides and the like.

The term "nucleic acid" means a polymer composed of nucleotides which can be deoxyribonucleotides or ribonucleotides. These compounds can be natural or synthetically produced deoxyribonucleotides or ribonucleotides. The synthetically produced nucleic acid can be of a naturally occurring sequence, or a non-natural unique sequence.

The term "nucleotide" means a monomeric unit comprising a sugar phosphate, usually ribose-5'-phosphate or 2'-deoxyribose-5'-phosphate covalently bonded to a nitrogen-containing base, usually, adenine (A), guanine (G), cytosine (C), or thymine (T) in the case of a deoxyribonucleotide, and usually, adenine (A), guanine (G), cytosine (C), or uracil (U) in the case of ribonucleotides.

Nucleic acids can hybridize with complementary nucleic acids in a sequence specific manner. That is they can participate in hybridization reactions in which the complementary base pairs A:T (adenine:thymine) and G:C (guanine:cytosine) form intermolecular (or intra-molecular) hydrogen bonds and cooperative stacking interactions between the planar neighboring bases in each strand through Pi electrons, together known as Watson-Crick base pairing interactions. The bases of the nucleic acid strands can also hybridize to form non-Watson-Crick base pairs by so-called "wobble" interactions in which G (guanine) pairs with U (uracil), or alternatively, I (inosine) pairs with C (cytosine), U (uracil) or A (adenine).

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "polynucleotide" or "nucleotide" refer to single or double stranded polymer composed of covalently nucleotide monomers forming a chain of generally greater than twenty to fifty nucleotides in length.

The term "phosphor particle" means a particle or composition comprising at least one type of upconverting phosphor material.

The term "primer" means a nucleotide with a specific nucleotide sequence which is sufficiently complimentary to a particular sequence of a target DNA molecule, such that the primer specifically hybridizes to the target DNA molecule.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "PCR" refers to a polymerase chain reaction. PCR is an amplification technology useful to expand the number of copies of a template nucleic acid sequence via a temperature cycling through melting, re-annealing and polymerization cycles with pairs of short primer oligonucleotides complementary to specific sequences bordering the template nucleic acid sequence in the presence of a DNA polymerase, preferably a thermostable DNA polymerase such as the thermostable Taq polymerase originally isolated from the thermophillic bacterium (*Thermus aquaticus*). PCR includes but is not limited to standard PCR methods, where in DNA strands are copied to provide a million or more copies of the original DNA strands (e.g. PCR using random primers: See for instance PCR with Arbitrary Primers: Approach with Care. W. C. Black IV, Ins. Mol. Biol. 2: 1-6 Dec. 2007); Real-time PCR technology, wherein the amount of PCR products can be monitored at each cycle (*Real time quantitative PCR*: C. A. Heid, J. Stevens, K. J. Livak and P. M. Williams, 1996 *Genome Research* 6: 986-994); Reverse transcription-PCR wherein RNA is first copied in DNA stands and thereafter the DNA strands are amplified by standard PCR reactions (See for example: *Quantitative RT-PCR: Pitfalls and Potential*: W. F. Freeman, S. J. Walker and K. E. Vrana; BioTechniques 26:112-125, January 1999).

The terms "ribonucleic acid" and "RNA" denote a polymer composed of ribonucleotides. The terms "deoxyribonucleic acid" and "DNA" denote a polymer composed of deoxyribonucleotides.

A "carrier nucleic acid" as used in this application means a bulk nucleic acid that can include large nucleic acid molecules, nucleic acid oligomers or nucleic acid fragments used as carrier for a DNA taggant having a unique identifiable sequence to identify or authenticate a particular product or to mark individuals present during fogging with the carrier nucleic acid. The carrier nucleic acid is generally present in a vast excess (w/w) over the amount of DNA taggant, so that isolation or even detection of the DNA taggant is impossible without prior knowledge of at least a portion of the uniquely identifiable sequence of the DNA taggant. Therefore, DNA taggant and the carrier nucleic acid may be likened to the proverbial "needle in a haystack" wherein the DNA taggant is the analog of the needle hidden in the haystack of carrier nucleic acid.

The term "person" may be defined as a homeowner, an employee, a shopper or other invitee, a licensee such as a repair person, or a trespasser or intruder.

Embodiments of the present invention are listed below as non-limiting examples illustrating the invention, but are not intended to be taken as limits to the scope of the present invention, which will be immediately apparent to those of skill in the art.

One embodiment of the present invention provides a method of marking an inventory item. The method includes providing an activatable smoke or fog generator and a reservoir for holding a marker smoke fluid and adapted to provide a flow of marker smoke fluid to the generator. The reservoir contains a marker smoke fluid including a carrier nucleic acid that includes DNA taggant having a uniquely identifiable sequence, and upon activation of the smoke generator, a marker smoke or fog is generated and caused to flow over the inventory item. The method further includes activating the smoke generator to produce the marker smoke including the carrier nucleic acid and DNA taggant so as to cause the marker smoke to flow over the inventory item and thereby to detectably mark the inventory item with DNA taggant.

Exemplary embodiments of the present invention also provide a security system. The security system includes a smoke generator, a reservoir for holding a marker smoke fluid and adapted to provide a flow of marker smoke fluid with carrier nucleic acid that includes a DNA taggant having a uniquely identifiable sequence to the smoke generator.

A fog machine or smoke machine is used in exemplary embodiments of the present invention to create a fog or smoke to mark the above-mentioned inventory items with the carrier nucleic acid that includes the DNA taggant having a uniquely identifiable sequence. The term "fog machine" and "smoke machine" may be used interchangeably throughout to mean the same thing. In addition, the terms "fog" and "smoke" may be used interchangeably throughout to mean the same thing.

The fog machine or smoke machine is, for example, a device which emits smoke such as a marker smoke for deterring intruders from remaining on the premises and which contains the carrier nucleic acid that includes a DNA taggant having a uniquely identifiable sequence for marking an inventory item and/or person present on the premises at the time of the activation of the smoke or fog generator with the carrier nucleic acid that includes the DNA taggant.

There are several different types of smoke or fog machines which can be used in accordance with exemplary embodiments of the present invention for generating marker smoke including a carrier nucleic acid that includes a DNA taggant. For example, suitable fog machines or smoke machines include water-based fog machines, oil based fog machines and chill fog machines. The present exemplary embodiment relates to water-based fog machines. However, as discussed below, in alternative embodiments of the present invention, oil based fog machines and chill fog machines can also be used.

For example, a water-based fog machine may include, for example, a fluid reservoir or tank, a pump (e.g. electric pump) to move the smoke fluid including carrier nucleic acid that contains the DNA taggant and a heat exchanger which vaporizes the smoke fluid with the DNA taggant. More complex models may include a variety of other features, including variable speed pumps to control the output of fog, timer modules, or components for remote operation and monitoring the status of the fog machine.

In the present exemplary embodiment, the water-based fog machine produces a marker smoke including the carrier nucleic acid that includes the DNA taggant having a uniquely identifiable sequence, which is a thermally generated white smoke specifically used as a security measure. This marker smoke including carrier nucleic acid that includes a DNA taggant having a uniquely identifiable sequence according to the present exemplary embodiment of the present invention may be created, in the water-based fog machine by, for example, vaporizing glycol (e.g., diethylene glycol, dipropylene glycol, propylene glycol, or triethylene glycol) or glycerine mixed with distilled water over a high temperature heat source and heated above its boiling range in the fog machine. The fog fluid in the fluid tank is forced through a heat exchanger by a high pressure pump. The heat exchanger maintains a high temperature at which the fluid vaporizes in a process commonly known as "flashing". As the fluid is "flashed" it rapidly expands, and that expansion forces the vapor through the nozzle of the machine.

Upon exiting the smoke or fog machine and coming into contact with the cooler air outside the fog machine, the vapor cools very rapidly and condenses, thereby rapidly forming a dense white fog composed of millions of microscopic liquid particles suspended in the air which obscures vision to the extent that even objects a few inches away are not readily visible and thus presents a confrontational barrier or obstacle to any intruders.

The very dense white appearance of the marker smoke or fog is caused by light refracting through the particles and scattering back. Because the particles produced are so small (varies from manufacturer to manufacturer, but typically range from an average diameter of, for example, about 0.2 microns to about 2.0 microns), the marker smoke or fog settles extremely slowly. In some embodiments, the marker smoke can last for an extended period after the smoke generator is shut down, and yet due to the very fine droplets, the marker smoke does not settle on surfaces to any discernable level and thus does not visibly contaminate exposed items or inventory.

In contrast to surveillance cameras and alarms systems, the marker smoke or fog immediately stops intruders in their tracks by obscuring from sight within seconds everything that could be stolen or vandalized, and disorienting the intruder or intruders. This leaves the intruder with few options other than to exit the building as quickly as possible. The marker smoke or fog, can be a non-toxic, glycol-based liquid which dissipates quickly with no residue and does not harm persons or paper or electronics. For example, in an exemplary embodiment, the fog machine or smoke machine is a water-based fog machine or smoke machine including a reservoir for holding the marker smoke fluid including the carrier nucleic acid and a DNA taggant having a uniquely identifiable sequence. The smoke generator which when activated disperses a security fog/marker smoke over the inventory items and any person in the vicinity of the inventory items. Security smoke or fog generators useful in the practice of the present invention include for example, SmokeCloak security fog generators (such as SmokeCloak Vali V20, SmokeCloak Vali V 10, SmokeCloak Vali V5, Smoke Cloak IPX range, Smoke Cloak Vali System 1000, SmokeCloak Vali System 2000, Smoke Cloak Vali System 3000, Smoke Cloak Vali System 4000, Smoke Cloak Vali System 4000 x-stream, Smoke Cloak Vali System 8000, SmokeCloak Vehicle Range System 24 from SmokeCloak, Denmark, FoQus, Protect 600, Protect 1100, Protect 220 from Protect A/S, Hasselager, Denmark, T-1500, T-1500X2, P-1500, P-1500X2 from Flash Fog Security, Ontario Canada, Bandit 240DB, 240PB from Bandit N/V, Opglabbeek, Belguim), or any other suitable water-based smoke or fog machines known to those of ordinary skill in the art.

In one embodiment, the smoke fluid stored in the reservoir of the device which is mixed with the carrier nucleic acid and DNA taggant for security/fog marker smoke is, for example, a water-based fluid including food or medical grade glycols and deionized water. These water-based smoke fluids include, for example, FL600-V and FL-600, from SmokeCloak, Denmark, XTRA+ from Protect A/S, Hasselager, Denmark, FlashFog from FlashFog Security, Ontario Canada, and HY-3 cartridge pack from Bandit 240DB, 240PB from Bandit N/V, Opglabbeek, Belguim or any other suitable smoke fluid known to those of ordinary skill in the art.

Alternatively, in another exemplary embodiment, the fog machine or smoke machine may be an oil-based fog machine or smoke machine. As with the above-mentioned glycol and water fog or smoke fluid, the carrier nucleic acid containing a DNA taggant is likewise included in these oil-based smoke fluids for marking purposes.

These oil-based smoke fluids may include, for example, mineral oil (for instance baby oil). Gas propelled smoke or fog machines use an inert gas (most commonly carbon dioxide or nitrogen) to propel the mineral oil into a heat exchanger where the smoke fluid is atomized and sent into the air to produce the marker smoke that incorporates the carrier nucleic acid that includes the DNA taggant. These oil-based smoke fluids which are converted into marker smoke or fog machines are similar in principle to smoke fluid created by glycol based smoke fluid except that the marker smoke of the oil-based marker smoke can withstand much higher temperatures and is much more dense than the marker smoke created by the glycol based marker fluids. Thus, oil-based smoke or fog is much denser and hangs in the air many times longer than water based fog, as the fog particles don't evaporate as quickly. As with glycol based marker smoke, oil-based marker smoke is perfectly safe, non-toxic, intrinsically biodegradable and does not leave a residue.

Suitable oil-based smoke or fog machines include for example Phantom PS31, Phantom PS 33 from Pea Soup Ltd., United Kingdom, Max 3000 APS Fog Generator, Max 5000 Fog APS Fog Generator, Max 5000 H.O. (High Output) APS Fog Generator from A.C.T. Lighting, Inc. at www.actlighting.com, and SG-OB30—Oil Based Smoke Generator Machine from Froggys Fog, Columbia, Tenn.

The oil-based smoke fluid may include, for example, MDG Neutral Fog Fluid from A.C.T. Lighting, Inc. at www.actlighting.com, PSSO180-5L: Smoke Oil 180, PSSO180-205L: Smoke Oil 180 from Pea Soup Ltd., United Kingdom, and Formula O Smoke Oil Fluid from www.froggysfog.com.

Alternatively, in still other embodiments, the security system may include other types of smoke or fog machines which do not use glycol based smoke fluid or mineral oil-based smoke fluid. Rather, these other embodiments may include chilled fog machines which create a low lying heavy fog that uses dry ice (i.e., solid carbon dioxide), or liquid nitrogen. In these embodiments, the carrier nucleic acid containing the DNA taggant is likewise included in the resulting fog. Unlike other types of smoke or fog machine, which create a smoke or fog that hangs in the air or rises, the fog created by dry ice or liquid is cold, and therefore sinks to the ground or to the lowest available level.

Suitable chilled smoke or fog machines for use in the practice of the present invention include, for example, Peasouper Dry Ice Fog Machine Le Maitre Pea Soupe and FreezeFog Pro Heavy Fog Chiller from Pea Soup Ltd., United Kingdom, Chauvet Nimbus Dry Ice Fog Machine, Product #: CVT NIMBUS LIST from Chauvet Lighting, Sunrise, Fla. City Theatrical SS6000 Dry Ice Fogger, Catalog # SFXF-0296 from Production Advantage, Inc, Williston, Vt.

In another exemplary embodiment, instead of a white colored smoke or fog being generated, the security system may further be coupled to a colored light element which is also activated when the smoke or fog generator is activated. In this embodiment, the colored light element when activated shines on the clear fog to such that the fog reflects the colored light rather than normal/white light to thereby produces a colored smoke or fog.

In addition to the above mentioned smoke or fog machines, any other device or smoke generator used to generate a smoke or fog may also be used in accordance with exemplary embodiment of the present invention. For example, in one embodiment, the DNA taggant may be provided in a canister or a smoke grenade, similar to that used by the military to create a smoke screen. These canisters are constructed of a metal cylinder with holes on the top and bottom that release smoke when ignited by the pulling of a pin or some other activation mechanism. Many smoke canisters contain dye that produces colored smoke when ignited. The smoke or fog can be produced a variety of colors, such as for example, red, purple, orange, yellow, blue, green, gray, white and black.

In an exemplary embodiment of the present invention, the smoke generators can be installed, for example, above ceilings or high on walls. In these embodiments, the smoke is forced vertically downwards and then rises forming a thickening barrier, which protects the smoke or fog generating device, itself, as well as the premises and contents.

In other embodiments, the smoke or fog machine may also be placed in any other suitable locations desired than those mentioned above. For example, the smoke or fog machine may be concealed within walls of the premises or placed within air ducts. In still other embodiments, the smoke or fog machine may be placed, for example, on the floor of the premises.

The security smoke or fog machines may be triggered by activation of an alarm system. For example, the security smoke or fog generators of the present exemplary embodiment may be part of an existing intruder alarm system. For example, once the alarm system detects a break-in to someone's premises, a heater element in the security fog generator converts liquid glycerol into an extremely dense artificial fog that is immediately spread throughout the area.

Alternatively, in an exemplary embodiment, the security smoke or fog system may be part of an independent system with dedicated detectors and an alarm panel which triggers the fog security generator device. This prevents the smoke or fog security system from activating if the intruder alarm is not confirmed, such as for instance a false alarm due to air movements e.g. movement caused by convection from an air conditioner detected by a motion sensor. These detectors are referred to as "hold-offs" in that they prevent the system from activating until movement is confirmed.

In one exemplary embodiment, in addition to the above deterrent effect provided by the marker smoke generated by the smoke or fog machine, the security system may further include additional deterrent accessories. For example, the security system may further include a bright, high intensity, flashing strobe light which amplifies the blinding effect of the marker smoke or fog. The rapidly flashing light prevents any attempts to see through the smoke or fog, and draws attention to the scene. In addition, the security system may further include, a sound device, such as, for example, a siren which emits an distracting, but harmless, noise that attracts attention and in combination with the marker smoke forces the intruder to flee immediately.

The security smoke or fog generator of the present exemplary embodiment may work immediately to protect a person's premises by preventing one or more intruders from taking and/or vandalizing property. For example, within seconds the intruder may be completely disoriented by the dense fog and immediately needs to leave the premises. Contrast this with the response time by the police and key holder (e.g. owner of the premises) which even in the best circumstances will take at least a few minutes. However, by the time they arrive to investigate the effects of the alarm activation, the intruders may already be gone and with property stolen from the premises. The security smoke or fog generators of the present exemplary embodiment rapidly inhibit the intruders from remaining on the premises and thereby minimize and/or prevent theft. In addition, since the fog discharged from the security fog generator of the present exemplary embodiment is a marker smoke or fog that includes a carrier nucleic acid containing a DNA taggant having a uniquely identifiable sequence, exposed areas of the intruder such as skin, hair and clothing as well as inventory items taken from the premises are marked with the carrier nucleic acid and DNA taggant and can be later identified by using authentication techniques to determine whether the person of interest and/or item where at the location at the time of the crime in question, as will be discussed in detail below.

For example, in an exemplary embodiment a person in the vicinity of the inventory item is exposed to the marker smoke or fog, the person having an exposed item of clothing and/or an exposed body surface, and thereby to detectably marking the exposed item of clothing and/or the exposed body surface of the person in the vicinity of the inventory item with marker smoke and carrier nucleic acid that includes the DNA taggant having a uniquely identifiable sequence. For example, the exposed areas of the human body which may be marked with the marker smoke generated by the security fog generator include, for example, the hair, skin, and nostrils. In addition, the exposed items of clothing of a person which may be marked with the marker smoke generated by the security smoke or fog generator may be any item of clothing, such as, for example, hats, gloves, jackets, coats, shirts, sweaters, pants, jeans, sweat pants, shorts, t-shirts, tank tops, suits, ties, dresses, skirts, swim wear, socks, shoes, sneakers, and boots.

In one embodiment, the detectably marked exposed item of clothing of a person may be any fabric or material, such as, for example, wool, cotton, linen, satin, rayon, viscose, polyester, nylon, acrylic, olefin, polyurethane, polylactide, plastic, leather, or an artificial fur or animal fur.

These security/marker smoke or fog generators of the present exemplary embodiment have a number of practical applications. For example, the security fog generator may protecting retailers of high value items, such as jewelers and banks. The security smoke or fog generator may also provide protection for ATM's and other areas where there are large amounts of cash. For example, the security smoke or fog generators may be used to protect businesses such as foreign exchange offices. These smoke or fog generators can also be used in private homes.

These security/marker smoke or fog generators are not restricted to applications in small premises, but rather can also be deployed to protect offices, warehouses, casinos, gas service stations. These may be large and isolated premises, where it can be difficult to provide a rapid response to intruders. The security smoke or fog generators of the present exemplary embodiment can be accurately deployed and triggered to protect valuable inventory items, while still allowing intruders to leave the premises.

In other exemplary embodiments of the present invention, the security/marker smoke or fog generators can also be installed in a vehicle for protection of the vehicle and the items contained therein. For example, this security/marker smoke or fog generator installed in a vehicle may be targeted to companies which transport desirable or high-value goods such as drugs, cigarettes, electronics, alcohol and cash.

Moreover, the dense smoke created by the security.marker smoke or fog generator is completely harmless. The smoke or fog may be created using, for example, the same principles as are used for smoke or fog machines in theatres, night clubs and discos.

The dense smoke or fog created by the security fog generator is suitable for virtually every environment as the fog is non-toxic and leaves no residue. This means that there is no damage to clothing, equipment, furnishings, machines, and it is safe to use in areas routinely used by staff, customers or even animals.

Even though the smoke is so dense that an intruder cannot see his/her hand in front of his/her face, it can take only about twenty minutes of airing to clear the room. Afterwards, one would not be able to tell that a smoke or fog protection system had been activated on the premises.

In addition, as the dense smoke emitted from the security smoke or fog generator includes a carrier nucleic acid that contains a DNA taggant having a uniquely identifiable sequence, the intruder's clothing, skin, hair, face, nostrils, hands, and/or inventory items taken by the intruder can be marked with the carrier nucleic acid and DNA taggant by the emitted smoke or fog such that the intruder and/or stolen object containing the carrier nucleic acid and DNA taggant can later be identified and authenticated. Thus, the security/marker smoke or fog generators of the present exemplary embodiment not only provide a deterrent against intruders and thieves from remaining on the premises, but also provide a way to later identify an intruder for criminal prosecution and/or identify an inventory item removed from the protected premises.

The inventors have surprisingly discovered that alkali treatment of isolated DNA also activates the DNA for covalent binding. Without wishing to be bound by theory, it is believed that alkaline conditions lead to ionization of the free hydroxyls at the 3' ends of the DNA strands. The negatively charged —O— group produced at the 3' end of the DNA is a strong nucleophile, reactive with positively charged groups to form stable covalent bonds, stably binding the DNA.

The invention provides methods of binding of a deoxyribonucleic acid to a substrate: The method includes exposing the deoxyribonucleic acid to alkaline conditions, and contacting the deoxyribonucleic acid to the substrate. The DNA bound to the substrate is available for binding by hybridization probes, PCR amplification and DNA sequencing methods.

In one embodiment, the alkaline conditions are produced by mixing the deoxyribonucleic acid with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the deoxyribonucleic acid that has been exposed to the alkaline conditions with the substrate. In one embodiment, the alkaline solution is a solution of a hydroxide of an alkali metal.

Another embodiment of the present invention provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of a hydroxide of an alkali metal and the alkali metal is selected from the group consisting of lithium (Li), sodium (Na), rubidium (Rb), and cesium (Cs).

Another embodiment of the present invention provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of an alkali metal hydroxide, wherein the alkali metal hydroxide is selected from the group consisting of lithium hydroxide (LiOH), sodium hydroxide (NaOH) and cesium hydroxide (CsOH). In one embodiment, the alkali metal hydroxide is sodium hydroxide (NaOH).

Another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide, wherein the alkali metal hydroxide solution having a concentration of from about 1 mM to about 1.0 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 10 mM to about 0.9 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 0.1 M to about 0.8 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 0.4 M to about 0.8 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of about 0.6 M.

Another embodiment of the present invention provides a method of binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9.0 to about 14.0 and incubated at a temperature of from about 0° C. to about 65° C. to produce the alkaline conditions.

Another embodiment of the present invention provides a method of binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9.0 to about 14.0 and incubated at a temperature of from about 5° C. to about 55° C. to produce the alkaline conditions.

Another embodiment of the present invention provides a method of increasing binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9 to about 14 and incubated at a temperature of from about 10° C. to about 45° C. to produce the alkaline conditions.

Another embodiment of the present invention provides a method of increasing binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9 to about 14 and incubated at a temperature of from about 15° C. to about 35 t to produce the alkaline conditions.

Another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide and incubating the mixture at a temperature of from about 0° C. to about 65° C.

Another embodiment of the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide and incubating the mixture at a temperature of from about 15° C. to about 22° C.

In another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of from about 0.1 M to about 1.0 M and incubating the mixture for a period of from about 1 minute to about 6 hours at a temperature of from about 10° C. to about 45° C.

In another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of from about 0.1 M to about 1.0 M and incubating the mixture for a period of from about 1 minute to about 6 hours at a temperature of from about 15° C. to about 25 t to produce the alkaline conditions.

Another embodiment provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of about 0.6 M and incubating the mixture for a period of from about 1 minute to about 6 hours at a temperature of from about 15° C. to about 35° C.

Another embodiment provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of about 0.6 M and incubating the mixture for a period of from about 10 minutes to about 2 hours at a temperature of from about 18° C. to about 22 t to produce the alkaline conditions.

In one embodiment, the present invention provides a method of binding a deoxyribonucleic acid to a substrate, the method includes exposing the deoxyribonucleic acid to alkaline conditions, wherein the alkaline conditions are produced by mixing the deoxyribonucleic acid with an alkaline solution having a high pH, incubating the mixture and then neutralizing the alkaline solution and contacting the neutralized solution containing the deoxyribonucleic acid that has been exposed to the alkaline conditions with the substrate. In one embodiment, the alkaline solution is a solution of a hydroxide of an alkali metal selected from the group consisting of lithium (Li), sodium (Na), rubidium (Rb), and cesium (Cs).

In another embodiment the present invention provides a method of binding a deoxyribonucleic acid to a substrate, the method includes exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution, and adding a molar excess of a polyionic polymer.

The polyionic polymer can be any suitable polyionic polymer. In one embodiment the polyanionic polymer is a polyamino acid. The polyamino acid can be a homopolymer of a natural amino acid such as L-lysine, or a homopolymer of a non-naturally occurring amino acid, such as for instance D-lysine. In one embodiment, the polyamino acid homopolymer is selected from the group consisting of polyputrescine, polycadaverine, polyspermidine, and polylysine.

Alternatively, in another embodiment, deoxyribonucleic acid can be mixed with a solution of any suitable high pH buffer to produce the alkaline conditions. The high pH buffer can be any suitable high pH buffer with a pKa in a range of from about 9.0 to about 11.0 or higher. In an embodiment, the pH of the high pH buffer can be, for example, a pH of about 9.0 or higher; a pH of about 10.0 or higher; or a pH of about 11.0 or higher. For example, in another embodiment, deoxyribonucleic acid can be mixed with a suitable high pH buffer such as CABS (4-[cyclohexylamino]-1-butanesulphonic acid) with a useful pH range of about 10.0-11.4 (at 25° C.) and a pKa of about 10.70 (at 25° C.) Product No. C5580 Sigma Aldrich, St. Louis, Mo.; CAPS (N-cyclohexyl-3-aminopropanesulfonic acid) with a useful pH range of about 9.7-11.1 (at 25° C.), a pKa of about 10.56 (at 20° C.), a pKa of about 10.40 (at 25° C.) and a pKa of about 10.02 (at 37° C.) Sigma Aldrich Product Nos. C6070 and C2632; AMP (2-amino-2-methyl-1-propanol) with a useful pH range of about 9.0-10.5 (at 25° C.), a pKa of about 9.70 (at 25° C.) Sigma Aldrich Product Nos. A9199 and A9879; CAPSO (N-cyclohexyl-2-hydroxyl-3-aminopropanesulfonic acid) with a useful pH range of about 8.9-10.3 (at 25° C.), a pKa of about 9.60 (at 25° C.), a pKa of about 9.43 (at 37° C.) Sigma Aldrich Product Nos. C2278 and C8085; CHES (2-(N cyclohexylamino)ethanesulphonic acid) with a useful pH range of about 8.60-10.0 (at 25° C.), a pKa of about 9.55 (at 20° C.), a pKa of about 9.49 (at 25° C.) and a pKa of about 9.36 (at 37° C.) Sigma Aldrich Product Nos. C2885 and C8210; AMPSO (3-[(1,1-dimethyl-2-hydroxyethyl)amino]-2-hydroxypropanesulfonic acid) with a useful pH range of about 8.3-9.7 (at 25° C.), a pKa of about 9.00 (at 25° C.), a pKa of about 9.10 (at 37° C.) Sigma Aldrich Product Nos. A6659 and A7585, to produce the alkaline conditions.

In an exemplary embodiment of the present invention, the deoxyribonucleic acid that has been exposed to the alkaline conditions is added as a component of a liquid composition. The liquid composition any be any suitable liquid composition, such as for instance, a printing ink. For example, in one embodiment, the ink may be a heat-curing epoxy-acrylate ink, such as Product No. 4408R or the 970 series Touch Dry® pellet each from Markem®, Keene, N.H. Alternatively, the Artistri® P5000+ Series-Pigment Ink from Dupont®, or an Epoxy Acrylate Ink, such as Product No. 00-988, from Rahn USA Corp. can be used.

The taggants of the present invention include, for example, nucleic acid taggants. Nucleic acid is a general term for deoxyribonucleic acid (DNA) or ribonucleic acid (RNA), and can be synthetic, or derived from an animal, a plant, a bacterium, a virus, a fungus, or a synthetic vector or a fragment of any of the above-listed nucleic acids, etc. It should be noted that a synthetic nucleic acid can have a sequence of a naturally occurring nucleic acid of an animal, plant, bacterium, fungus, virus or any other organism or synthetic vector. Alternatively, a synthetic nucleic acid can have a unique sequence not found in nature. It should be understood that such unique non-natural sequences may have stretches of sequences which are found in nature, but the entire non-natural sequence is unique and is not found in any plant, animal or virus or any other natural organism. In particular, the nucleic acid sequence encoding the element of data or indicia encrypted or encoded in the taggant of the invention is a unique, non-natural sequence and thereby is adapted for use in authentication of an object of interest.

The taggant useful in combination with the bound DNA that has been activated by alkaline treatment according to the present invention can be any suitable detectable or traceable taggant, for example, a chemical marker or a biological marker. In an embodiment of the methods of the present invention, the taggant is selected from a UV fluorophore, a ceramic IR marker, other DNA, an amino acid, a peptide, a protein, a lipid, a sugar, a polysaccharide, a pheromone, a scent, a trace element, a rare earth element, or a combination of any two or more thereof.

In an embodiment of the present invention, the taggant includes a nucleic acid. In one embodiment, the taggant consists essentially of DNA and no other significant component useful for identification or authentication.

Alternatively, or in addition, other taggants such as, for example, ultraviolet (UV) taggants, Up Converting Phosphor (UCP) infrared (IR) taggants, UV marker taggants, UV fluorophore taggants, ceramic IR marker taggants, protein taggants, and/or trace element taggants can be used in combination with deoxyribonucleic acid taggants activated by alkaline treatment according to the methods of the present invention. In an exemplary embodiment, the taggants used may include, for example, a combination of DNA taggants, and an IR upconverting phosphor (UCP) taggant. In another exemplary embodiment, the taggants used may include, for example, a combination of DNA taggants, an IR upconverting phosphor (UCP) taggant and a UV taggant. For example, in an exemplary embodiment, the IR (UCP) taggant can be, for example, a green, a blue or a red (UCP) IR taggant, such as for instance the Green IR Marker, Product No. BPP-1069; the Blue UCP, Product No. BPP-1070; or the Red UCP, Product No. BPP-1071 from Boston Applied Technologies Inc., Woburn, Mass.

The solution in which the soluble taggants are dissolved according to the methods of the present invention can include, for example, water, TE buffer (10 mM Tris-HCl, 1 mM EDTA), Tris-glycine buffer, Tris-NaCl buffer, TBE buffer (Tris-borate-EDTA), TAE buffer (Tris-acetate-EDTA) and TBS buffer (Tris-buffered saline), HEPES buffer (N-(2-Hydroxyethyl)piperazine-N'-ethanesulfonic acid), MOPS buffer (3-(N-Morpholino)propanesulfonic acid), PIPES buffer (Piperazine-N,N'-bis(2-ethanesulfonic acid), MES buffer (2-(N-Morpholino)ethanesulfonic acid), PBS (Phosphate Buffered Saline), PBP buffer (sodium phosphate+EDTA), TEN buffer (Tris/EDTA/NaCl), TBST buffer (Tris-HCl, NaCl, and Tween 20), PBST buffer (Phosphate Buffered Saline with Tween 20) and any of the many other known buffers used in the biological and chemical sciences.

The objects of interest marked with the deoxyribonucleic acid and optional additional taggants according to exemplary embodiments of the present invention include, for example, ceramic surfaces, plastic films, vinyl sheets, antiques, items of jewelry, identification cards, credit cards, magnetic strip cards, paintings, artwork, souvenirs, sports collectibles and other collectibles. The authenticity of these objects can then be verified by identifying the taggants bound or covalently bonded thereon through, for example, methods described in further detail below.

In one embodiment, the surface to which the deoxyribonucleic acid that has been exposed to alkaline conditions is bound can be the surface of an object or item formed of a polymer, such as a polymer selected from the group consisting of polycarbonate (PC), polymethyl methacrylate (PMMA), polyurethane (PU), polystyrene (PS), nylon or polypropylene (PP) all of which are readily commercially available.

In one embodiment, the method of the present invention further includes binding an object with the deoxyribonucleic acid that has been exposed to alkaline conditions according to the methods of the present invention, the deoxyribonucleic acid such that the activated deoxyribonucleic acid is chemically bonded to the object, thereby providing the object with authentication, tracking and anti-counterfeiting functions.

The deoxyribonucleic acid that has been exposed to alkaline conditions that has been applied onto an object provides a traceable deoxyribonucleic acid taggant. The traceable deoxyribonucleic acid taggant can be applied over all or part of the object to be identified, validated, authenticated, or if the object is an item of commerce, the item can be tracked at any point through the stream of commerce.

In another embodiment, the traceable deoxyribonucleic acid is an alkaline pH activated DNA bound to the object.

In another embodiment, the alkaline pH activated DNA is bound to an object including a material selected from the group consisting of cotton, wool, nylon, plastic, metal, glass, wood, printing ink, and a pharmaceutical powder.

In another embodiment, the alkaline pH activated DNA is bound to a plastic material selected from the group consisting of a polycarbonate (PC), a polymethyl methacrylate (PMMA), a polyurethane (PU), a polystyrene (PS), a polyamide, a polypropylene (PP), a polyvinyl chloride (PVC), polysulphone, polyvinilacetate (PVA), polyester (PES), a polyethylene terephthalate (PET), a polyethylene (PE), a benzocyclobutene (BCB), a high-density polyethylene (HDPE), a polyvinylidene chloride (PVDC), a low-density polyethylene (LDPE), a high impact polystyrene (HIPS), an acrylonitrile butadiene styrene (ABS), a phenol formaldehyde resin (PF), a melamine formaldehyde (MF), a polyetheretherketone (PEEK), a polyetherimide (PEI), polyimide (PI), a polyether ketone imide, a polylactic acid (PLA), a polytetrafluoroethylene (PTFE), a polymethyl pentene (PMP), a polyether ketone (PEK), a polyether sulfone (PES), a polyphenylene sulfide (PPS), a polytetrafluoroethylene (PTFE), a fluropolymer, a silicone, an Ionomer, a moldable elastomer, an ethylene vinyl alcohol (EVOH), a methalocene polymer and a polyethylene naphthalate material.

In one embodiment, the object marked with the traceable deoxyribonucleic acid includes a pharmaceutical composition comprising a pharmaceutical tablet, a pharmaceutical capsule, or a pharmaceutical powder.

Another exemplary embodiment of the present invention provides a method for authenticating an object which includes providing an object to which a taggant is bound or covalently bonded, sampling the object for identification, tracking, or verifying the authenticity of the object by identifying the unique traceable deoxyribonucleic acid (DNA) taggant. In one embodiment, the unique taggant is a DNA taggant having a unique DNA sequence and the unique DNA sequence is stored in a database that matches the unique DNA sequence to the data elements corresponding to the object which is bound to or covalently bonded to the unique taggant. The database can in turn be located on a computer that can be accessed in order to locate, track, authenticate and verify the identity of the tagged object from which the taggant was detected.

DNA taggants useful in the examples described below include any suitable DNA taggant, such as for instance, in one embodiment, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs. Alternatively, the DNA taggant can be single-stranded DNA or any suitable length, such as between about 40 bases and about 1000 bases; between about 80 and 500 bases; or between about 100 and about 250 bases. The DNA taggant can be natural DNA, whether isolated from natural sources or synthetic; or the DNA taggant can be a synthetically produced non-natural sequence. All or a portion of the DNA may comprise an identifiable sequence.

In one exemplary embodiment, the DNA taggant is identifiable by any suitable detection and/or identification method such as for example, hybridization with a taggant-sequence specific nucleic acid probe, an in situ hybridization method (including fluorescence in situ hybridization: FISH), amplification using a polymerase chain reaction (PCR), such as quantitative/real time PCR and detection of the amplified sequences (amplicons) by any of the variety of standard well known methods.

In another embodiment, the hybridization can be carried out with DNA probes, each having a specific nucleotide sequence capable of hybridizing with its complementary sequence. Different probes may be included, one to each cell or well of an array or matrix so that only the probe having the complement to the DNA taggant will hybridize and generate a detection signal at the unique location of the complementary probe. Alternatively, if the complementary probe is present in several cells of wells arranged in a particular pattern, then hybridization with the complementary DNA taggant sequence will be detected in the precise pattern of the specific probes in the array or matrix. For example, in the PCR identification method, the nucleic acid taggants, e.g., DNA taggants recovered from the object are amplified by polymerase chain reaction (PCR) and resolved by gel electrophoresis. Since the sequence of the nucleic acid taggants of the present invention are unique and specific to the tagged object, the original nucleic acid will be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant. In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is vanishingly small. Therefore, by comparing the sizes of PCR products, the authenticity of labeled objects can be verified, non-authentic objects can be screened and rejected and anti-counterfeit screening purpose is then achieved.

The number of amplicons amplified and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels and the electrophoretic separation can be in a slab gel or by capillary electrophoresis.

Alternatively, the deoxyribonucleic acid that has been exposed to alkaline conditions that has been bound to the item or surface of interest can be subjected to PCR, the PCR amplicons can be recovered and sequenced according to well known routine nucleic acid sequencing techniques.

The carrier nucleic acid (NA) that includes the DNA taggant having a uniquely identifiable sequence that is incorporated into the smoke fluid of the smoke or fog generator maybe natural DNA, synthetic DNA, cDNA, or other DNA material, or any other nucleic acid fragment comprising DNA or DNA derivatives. The carrier nucleic acid may include nucleic acid fragments that are single stranded or double stranded and may vary in length. The DNA taggant having a uniquely identifiable sequence can be any DNA having a uniquely identifiable sequence. For instance, the DNA having a uniquely identifiable sequence can be a totally synthetic DNA, a semi-synthetic DNA wherein a natural DNA fragment or fragments are rearranged and religated to produce the uniquely identifiable sequence, or wherein the natural DNA fragment or fragments are extended or ligated with one or more bases, one or more synthetic oligonucleotides or one or more polynucleotides to produce a DNA taggant having a uniquely identifiable sequence. All such uniquely identifiable sequences are non-natural sequences.

In one embodiment the DNA taggant can include more than one uniquely identifiable sequence each of which can be separately identified detecting a specific amplicon product of a polymerase chain reaction (PCR) using a primer pair specific for the particular unique sequence. The identification can be by any suitable method, such as for instance by sequence determination, by specific hybridization using one or more sequence specific probes or by determination of the length of the PCR amplicon in base pairs after gel electrophoresis or capillary electrophoresis. In another alternative, when the DNA taggant includes two or more uniquely identifiable sequences, the identification can be by PCR and determination of the length of each of the PCR amplicons in base pairs, wherein each uniquely identifiable sequence and complementary primer pair are chosen to produce an amplicon of a different specific base pair length. The amplicons can then be resolved and identified on the basis of the lengths of each of the amplicons produced from the uniquely identifiable sequences of the DNA taggant.

The carrier nucleic acid may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified and randomly relegated to produce suitable maker nucleic acid having non-natural sequences. The length of the nucleic acid marker/tag usually ranges between about 100 to about 10 kilo bases, more usually about 500 bases to about 6 kb, and preferably about 1 kb to about 3 kb in length. In some embodiments, the form of the DNA may be linear or circular with sizes ranges from a few bases (5 bases) to genomic DNA (1 million to 30 billion base pairs).

In an exemplary embodiment, the uniquely identifiable sequence of the DNA taggant is a sequence of from about 25 bases to about 10,000 bases long. In another exemplary embodiment, the uniquely identifiable sequence of the DNA taggant is a sequence of from about 50 bases to about 5,000 bases long. In another exemplary embodiment, the uniquely identifiable sequence of the DNA taggant is a sequence of from about 75 bases to about 500 bases long. In another exemplary embodiment, the uniquely identifiable sequence of the DNA taggant represents less than one part per ten thousand of the carrier nucleic acid. In another exemplary embodiment, the uniquely identifiable sequence of the DNA taggant represents less than one part per hundred thousand of the carrier nucleic acid. In another exemplary embodiment, the uniquely identifiable sequence of the DNA taggant represents less than one part per million of the carrier nucleic acid.

The carrier nucleic acid is included in the smoke fluid of the security/marker smoke or fog generator to mark an inventory item and/or a person in the vicinity of the inventory item when the smoke or fog generated containing the carrier nucleic acid including the DNA taggant is released onto the inventory item and/or person.

In the present exemplary embodiment, DNA is the carrier nucleic acid included in the marker smoke fluid of the security smoke or fog generator to mark an inventory item and/or a person in the vicinity of the inventory item when the smoke or fog is generated. However, in an alternative exemplary embodiment, other nucleic acids such as, for example, RNA or a DNA:RNA hybrid may be used as the carrier nucleic acid containing the DNA taggant in the smoke fluid instead of or in addition to DNA as the carrier nucleic acid.

In the present exemplary embodiment, the DNA taggant included in the carrier nucleic acid may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a DNA taggant may make detection of the marker easier and quicker, the use of a plurality of nucleic acid sequences such as STR and SNP, in general, give a higher degree of confidence in a positive identification.

For exemplary purposes, the nucleic acid concentration may vary from pico grams per liter ($1 \times 10^{-12}$ gram/L) to micro grams per liter ($1 \times 10^{-9}$ gram/L). In certain embodiments, the DNA concentration may range from 1 ppb (parts per billion) to 500,000 ppb (i.e. 500 ppm). An important feature of the carrier nucleic acid is to protect the DNA taggant having the uniquely identifiable sequence from UV and other influences that may cause degradation over time.

In certain other embodiments of the methods of the invention, the carrier nucleic acid is derived from DNA extracted from a specific plant source and rendered non-functional with scrambled sequences. For example, the DNA may be specifically digested and ligated to generate artificial nucleic acid sequences which are unique and previously unknown to the world. The digestion and ligation of the extracted DNA is completed by standard restriction digestion and ligase techniques known to those skilled in the art of molecular biology. Once the modified DNA taggant has been produced, the taggant can be encapsulated into materials for protection against UV and degradation. The DNA encapsulant material can be any suitable encapsulant material, such as for instance an encapsulant material of plant origin.

In certain embodiments, when the DNA taggant can be encapsulated and suspended in a solvent solution (aqueous or organic solvent solution) producing a "stock" DNA taggant solution at a specified concentration. This stock DNA taggant solution can then easily be added to carrier nucleic acid at an appropriate concentration for incorporation into a marker smoke fluid or marker fog fluid. In certain instances, the DNA taggant maybe mixed with other components without any prior encapsulation. Several processes such as nucleic acid fragment encapsulation and other techniques utilized for protecting nucleotides, and in particular, DNA from degradation, are well known in the art.

In other embodiments, the carrier nucleic acid can camouflage or "hide" the specified nucleic acid tag with extraneous and nonspecific nucleic acid oligomers or fragments, thus making it difficult for unauthorized individuals to identify the sequence of the DNA taggant. In certain embodiments, the carrier nucleic acid comprises a specified double stranded DNA of known sequence from a known source (e.g. mammal, invertebrate, plant sources and the like) along with genomic DNA from the corresponding or similar DNA source. The amount of the DNA taggant to be incorporated into a carrier nucleic acid varies depending on the particular marker smoke to be used and the setting where the marker smoke generator is to be deployed, the duration that the taggant needs to be viable (e.g. 1 day, 1 month, 1 year, multiple years) prior to identification, expected environmental exposure, the detection method to be utilized, and so forth.

After carrier nucleic acid containing the DNA taggant with a uniquely identifiable sequence has been manufactured or isolated, the preparation of carrier nucleic acid containing the DNA taggant is then mixed with the smoke fluid and then the mixture is stored in the reservoir of the smoke or fog generator.

The marker smoke fluid mixture including the carrier nucleic acid and the DNA taggant is then converted by the smoke generator to produce a marker smoke comprising the carrier nucleic acid and the DNA taggant so as to cause the marker smoke to flow over the inventory item and any person in the vicinity of the inventory item, the person having an exposed item of clothing and/or an exposed body surface, and thereby to detectably mark the inventory item with the DNA taggant, and detectably mark the exposed item of clothing and/or the exposed body surface of any person present in the vicinity of the inventory item and within range of the marker smoke with the DNA taggant having a uniquely identifiable sequence.

The carrier nucleic acid containing the DNA taggant having a uniquely identifiable sequence that is included in the marker smoke can then be detected, recovered and authenticated from the inventory item and/or person exposed to the marker smoke using the following techniques discussed below.

In general, PCR is an useful technique for detection of the DNA taggant as described below. The copy number of DNA taggant in a predetermined sample size of carrier nucleic acid used in marker smoke fluid is about 3 copies to about 100,000 copies, more usually about 10 copies to about 50,000 copies, and even more usually about 100 copies to about 10,000 copies of DNA taggant. The concentration of carrier nucleic acid including the DNA taggant incorporated into the smoke fluid of the security smoke or fog generator may be varied as required depending upon particular embodiments of the invention.

In certain embodiments the placement or position of the DNA taggant on the human body of a person and/or on the inventory item of interest maybe located by the detection of materials or compounds configured to be optically detectable and may be associated with the DNA taggant in the carrier nucleic acid. For example, in many embodiments the DNA taggant may be bound or coupled to, or otherwise associated with, a chemically or optically detectable label. Detection of DNA-labeled portions of the item may be carried out by optically detecting fluorescent dyes or upconverting phosphor particles which can be detected easily by UV and/or IR portable light sources. Thus, for example, a hair sample, clothing sample or a sample from the inventory item could be examined with a UV or IR light source to find a particular region or regions of the sample (e.g., hair sample, clothing sample or a sample from the inventory item) that contain a particular fluorescent marker. In this manner, only a small portion of the item (as identified by the fluorescent dye or particles) needs to be sampled for detection of the DNA taggant sequence. The materials or compounds utilized for locating the position of the carrier DNA on the sample of interest maybe coated with functional groups which can covalently bind to the carrier nucleic acid and the DNA taggant, as described below.

In general, analyzing the collected sample (e.g. hair sample, clothing sample, inventory item sample) for the presence of DNA taggant may include, for example, providing a "detection molecule" configured to detect the DNA taggant. The detection molecule can be, but is not limited to a nucleic acid probe and/or primer set which is complementary to the sequence of the DNA taggant, or a dye label or color producing molecule configured to selectively bind and adhere to the DNA taggant, for instance by being covalently linked to a sequence of bases to at least a portion of the uniquely identifiable sequence of the DNA taggant. When a PCR method is used in the detection of the DNA taggant including amplifying the DNA taggant, the detection molecule(s) are primers which specifically bind to a certain sequence of the DNA taggant. When real time PCR is utilized in the analysis of the sample, an identifiable nucleotide probe may also be provided to enhance the detection of the DNA taggant as well as provide semi-quantitative or quantitative authentication results. With the use of real time PCR, results from the analysis of the sample can be completed within 30 minutes to 2 hours, including extracting or purifying the carrier nucleic acid that includes the DNA taggant from the collected sample. Various embodiments utilize a wide range of detection methods besides for PCR and real time PCR, such as fluorescent probes, probes configured to molecules which allow for the detection of the nucleic acid tag when bound to the probe by Raman spectroscopy, infrared spectroscopy or other spectroscopic techniques used by those skilled in the art of nucleic acid detection.

The results of the analysis of the collected sample are then analyzed to determine if the specific DNA taggant was detected in the sample. If the specific DNA taggant is detected in the sample, the collected sample of the inventory item is authenticated as genuine. If the DNA taggant is detected in the collected sample of interest, the conclusion from the analysis is that person is not a match or cannot be verified as present during the activation of the marker smoke or fog machine.

Thus, among the methods of detection for the DNA taggant on the article of clothing or exposed skin or hair of the a person of interest or on an inventory item, the DNA taggant may be linked to or otherwise associated with an optical reporter material for quick detection of the position of the carrier nucleic acid containing the DNA taggant on the article of clothing or exposed skin or hair of the a person of interest or on an inventory item. For forensic DNA identification, DNA is extracted from DNA labeled objects and subjected to PCR amplification with specific primers to produce amplicons that can be analyzed by any of a number of well known means such as for instance by either gel electrophoresis or capillary electrophoresis. Alternatively, RT-PCR amplification and detection by fluorescent reporters or any suitable detection means known in the art may be used to obtain results within a very short period of time.

In some embodiments, the quantity or concentration of the DNA taggant within the carrier nucleic acid in a collected sample can be determined and compared to the initial amount of carrier nucleic acid containing the DNA taggant placed in the product to allow for the detection of fraud caused by diluting the product with inferior products by forgers. In general, quantitative detection methods comprise providing an internal or external control to evaluate the efficiency of detection from one sample/analysis to the next. The efficiency of detection may be affected by many parameters such as, probe hybridization conditions, molecules or substances in the product which may interfere with detection, and/or primer integrity, enzyme quality, temperature variations for detection methods utilizing PCR. By providing a control, in the detection methods, any variable conditions can be normalized to obtain an accurate final concentration of the DNA taggant in the carrier nucleic acid present on the product.

Incorporation of Detectable Moieties

In certain embodiments, the carrier nucleic acid that includes the DNA taggant is labeled with at least one compound or "detection molecule" prior to being incorporated into the smoke fluid in the extraction and/or detection of the carrier nucleic acid from an inventory item or a sample from the person of interest who may have been exposed to the marker smoke including the carrier nucleic acid containing the DNA taggant. A detection molecule is a molecule or compound with at least one functionality. For example, fluorescent molecules, which may be in particulate form (e.g. an upconverting phosphor: UCP), may be configured to the carrier nucleic acid for certain detection methods which are described in detail below.

In certain embodiments, suitable dyes include, but are not limited to, coumarin dyes, xanthene dyes, resorufins, cyanine dyes, difluoroboradiazaindacene dyes (BODIPY), ALEXA dyes, indoles, bimanes, isoindoles, dansyl dyes, naphthalimides, phthalimides, xanthenes, lanthanide dyes, rhodamines and fluoresceins. In other embodiments, certain visible and near IR dyes and IR materials are known to be sufficiently fluorescent and photostable to be detected as single molecules. The visible dye, BODIPY R6G (525/545), and a larger dye, LI-COR's near-infrared dye, IRD-38 (780/810) can be detected with single-molecule sensitivity and can be used to practice the authentication process described herein. In certain embodiments, suitable dyes include, but are not limited to, fluorescein, 5-carboxyfluorescein (FAM), rhodamine, 5-(2'-aminoethyl) aminonapthalene-1-sulfonic acid (EDANS), anthranilamide, coumarin, terbium chelate derivatives, Reactive Red 4, BODIPY dyes and cyanine dyes.

There are many suitable linking moieties and methodologies for attaching fluorophore or visible dye moieties to nucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' amino-alkylphosphoryl group); AP3 Labeling Technology (U.S. Pat. Nos. 5,047,519 and 5,151,507, assigned to E.I. DuPont de Nemours & Co); Agrawal et al, Tetrahedron Letters, 31: 1543-1546 (1990) (attachment via phosphoramidate linkages); Sproat et al., Nucleic Acids Research, 15: 4837 (1987) (5' mercapto group); Nelson et al, Nucleic Acids Research, 17: 7187-7194 (1989) (3' amino group); and the like.

In other embodiments, a nucleic acid probe complementary to the DNA taggant within the carrier nucleic acid is labeled with at least one compound or molecule with functionality to aid in the detection of the carrier nucleic acid or the DNA taggant. The techniques and dyes utilized in labeling the nucleic acid tag or the complementary probe are the same due to the nucleic acid nature of the tag and probe.

The detection molecules of the invention can be incorporated into probe motifs, such as Taqman probes (Held et al., Genome Res. 6: 986-994 (1996), Holland et al., Proc. Nat. Acad. Sci. USA 88: 7276-7280 (1991), Lee et al., Nucleic Acids Res. 21: 3761-3766 (1993)), molecular beacons; Tyagi et al., Nature Biotechnol., 16:49-53 (1998), U.S. Pat. No. 5,989,823, issued Nov. 23, 1999)) scorpion probes (Whitcomb et al., Nature Biotechnology 17: 804-807 (1999)), sunrise probes (Nazarenko et al., Nucleic Acids Res. 25: 2516-2521 (1997)), conformationally assisted probes (Cook, R., copending and commonly assigned U.S. Provisional Application No. 60/138,376, filed Jun. 9, 1999), peptide nucleic acid (PNA)-based light up probes (Kubista et al., WO 97/45539, December 1997), double-strand specific DNA dyes (Higuchi et al, Bio/Technology 10: 413-417 (1992), Wittwer et al, Bio/Techniques 22: 130-138 (1997)) and the like. These and other probe motifs with which the present detection molecules can be used are reviewed in Nonisotopic DNA Probe Techniques, Academic Press, Inc. 1992.

In other embodiments, the molecular beacon system is utilized to detect and quantify the DNA taggant from the item of interest. "Molecular beacons" are hairpin-shaped nucleic acid detection probes that undergo a conformational transition when they bind to their target that enables the molecular beacons to be detected. In general, the loop portion of a molecular beacon is a probe nucleic acid sequence which is complementary to the target nucleic acid to be detected. The stem portion of the molecular beacon is formed by the annealing of arm sequences of the molecular beacon that are present on either side of the probe sequence. A functional group such as a fluorophore (e.g. coumarin, EDNAS, fluorescein, lucifer yellow, tetramethylrhodamine, texas red and the like) is covalently attached to the end of one arm and a quencher molecule such as a nonfluorescent quencher (e.g. DABCYL) is covalently attaches to the end of the other arm. When there is no target (such as the DNA taggant of the invention) present, the stem of the molecular beacon keeps the functional group quenched due to its close proximity to the quencher molecule. However, when the molecular beacon binds to their specified DNA taggant target, a conformational change occurs to the molecular beacon such that the stem and loop structure cannot be formed, thus increasing the distance between the functional group and the quencher which enables the presence of the DNA taggant target to be detected. When the functional group is a fluorophore, the binding of the molecular beacon to the DNA taggant is detected by fluorescence spectroscopy.

In certain embodiments, a plurality of nucleic acid tags with varying sequences are used in labeling a particular product. The different DNA taggants can be detected quantitatively by a plurality of molecular beacons, each with a different colored fluorophore and with a unique probe sequence complementary to at least one of the plurality of nucleic acid tags. Being able to quantitate the various fluorophores (e.g. various DNA taggants) provides a higher level of confidence of identification. It should be noted, that the other functional groups described above useful in labeling nucleic acid probes can also be utilized in molecular beacons for the present invention.

In other embodiments, the methods for authenticating an inventory item or sample from a person of interest, may comprise labeling the item with an optical reporter marker linked to a carrier nucleic acid containing a DNA taggant, detecting the optical reporter, and then characterizing or verifying the DNA taggant associated with the item in an effective manner, by nucleic acid sequencing, hybridization or other such techniques.

For example, in an exemplary embodiment, an optical reporter marker having a nucleic acid taggant linked to an optical reporter particle, the carrier nucleic acid containing a DNA taggant having a known portion of its sequence identifiable or sequenceable. In another embodiment, the optical reporter is included in the marker smoke fluid but is not linked to the carrier nucleic acid containing the DNA taggant.

The optical reporter particle may be, for example, a light emitting optical reporter such as, for example, an upconverting phosphor particle (UCP). In certain embodiments the upconverting phosphor particle UCP is coated with a silylation composition which is configured to be covalently linked to the carrier nucleic acid including the DNA taggant. UCPs and other optical reporters such as those described in U.S. patent application Ser. No. 11/954,038, filed Dec. 11, 2007, U.S. patent application Ser. No. 11/954,051, filed Dec. 11, 2007, U.S. patent application Ser. No. 11/954,030, filed on Dec. 11, 2007, and U.S. patent application Ser. No. 11/954,055, filed on Dec. 11, 2007, the disclosures of which are each incorporated by reference herein in their entireties may be used in the smoke fluid in combination with the carrier nucleic acid that contains the DNA taggant having a uniquely identifiable sequence to locate the DNA taggant sequence in a sample exposed to the marker fog or smoke.

In another exemplary embodiment, the optical reporter used in combination with the carrier nucleic acid may be an ultraviolet (UV) taggant, a long UV marker or a UV fluorophore. In yet another embodiment, the optical reporter used in combination with the carrier nucleic acid may supplemented or replaced by a protein, and/or a trace element.

The optical reporter compound may be produced as a solid or liquid, water or oil based, a suspension, an aggregate or the like. The optical reporter marker allows for easy detection of where the optical reporter marker is located on or within the item of interest with basic high intensity light emitting equipment such as a hand-held ultraviolet (UV) lamp, IR emitting diode, hand-held IR laser and the like.

The optical reporter marker also enables the authentication of the item of interest by both confirming that the correct emission spectra/wavelength for the optical reporter particle is detected as well as being able to locate and determine by sequencing if the DNA taggant comprises the correct uniquely identifiable nucleic acid sequence.

The nucleic acid-linked optical reporter marker which includes the nucleic acid-linked optical reporter marker may be mixed with the marker smoke fluid of a security/marker smoke or fog for authenticating an inventory item of interest or a sample collected from a person of interest. The nucleic acid-linked optical reporter marker may be applied in a specific, pre-determined amount or quantity. The marker is may be applied in the form of a dense smoke or fog which is emitted from the security smoke or fog generator due to activation of the heat generator of the security/marker smoke or fog generator. In particular, a heater element in the security/marker smoke or fog generator may be activated by a triggering event such as, e.g., a security alarm to convert liquid glycerol of the marker smoke fluid into an extremely dense artificial smoke or fog which includes the optical reporter marker and which is immediately spread throughout the area including on a exposed areas of a person (e.g., hair, skin, nostrils, and/or clothing) in the vicinity of the fog generator and on inventory items located in the area. Thus, exposed areas of the person and/or the inventory item may be marked with the nucleic acid-linked optical reporter marker and the nucleic acid-linked optical reporter emitted in the dense fog may then later be used for authentication purposes to determine whether the person of interest was at the location of the security/marker smoke or fog generator and/or whether the item was also at that location at the time of activation of the security/marker smoke or fog generator.

For the purpose of detecting the nucleic acid-linked optical reporter tag associated with the person and/or item of interest. Often, the detecting of the optical reporter marker associated with the item occurs after a period of time has lapsed. For example, after marking of the missing item, the item may be introduced into a supply chain or the item may be placed into service. Having a method in which the original owner can track and authenticate items or goods allows for a better monitoring of when and where stolen goods are being sold.

Detecting the optical reporter particle(s) represents a first level of authentication of the item of interest. When the optical reporter particle is an upconverting phosphor particle, the marker can be detected by a high energy invisible light source such as an infrared laser, which may be hand-held and manipulated by a user, or suitably mounted to allow goods to be positioned in the lamp output. The infrared light is absorbed by the optical reporter particles, which in turn emit light at a wavelength that is characteristic of the optical reporter particle. Various upconverting phosphor (UCP) compositions that provide selectable output wavelengths are known in the art, as described further below, and may be used with the invention. Once the optical reporter has been located within or on the inventory item of interest or an item from the person of interest, the obtaining of a sample of the optical reporter marker may occur.

A sample is collected from the item of interest having the optical reporter marker as described below. In certain embodiments, this may comprise visually inspecting the item for an optical reporter signal under the appropriate illumination, and/or scraping, cutting or dissolving a portion of the marked item to obtain a sample for more detailed analysis. The collecting of the sample may be carried out, for example, by wiping the item with a cloth or cotton swab (which may be moistened with solvent) to recover the optical reporter marker and associated DNA taggant from the item. In another embodiment, the optical reporter marker may be recovered from the item using, for example, medical tape. In still other embodiments, sample collection may be achieved using a cutting, gouging, scraping, abrading, or other such sampling methods, for instance with tool configured to remove a portion of the item containing the optical reporter marker.

Once the presence and located of the optical reporter are detected the collected sample may then be analyzed for the presence of the carrier nucleic acid that includes the DNA taggant having a uniquely identifiable sequence. In some embodiments the collected sample are can be analyzed by determining the DNA sequence of the DNA taggant, and comparing the determined DNA sequence with a known or reference DNA sequence of the DNA taggant. The analysis of the sample collected from the item may occur without further purification, but in many embodiments some form of extraction, isolation or purification of the nucleic acid tag obtained in the sample may be required. Details on the extraction, concentration and purification techniques useful for the methods of the invention are described more fully below and also in the examples.

In general, analyzing the sample includes providing a "detection molecule" complementary to the DNA taggant. A detection molecule includes but is not limited to a nucleic acid probe and/or primer set which is complementary to at least a portion of the sequence of the DNA taggant, or a dye label or color-producing molecule configured to bind and adhere to the DNA taggant. The detection of the nucleic acid taggant may further comprise amplifying the DNA taggant using PCR, with the detection molecule(s) being primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or fully quantitative authentication results. With the use of real time PCR, results from the analysis of the sample can be completed within 30 minutes to two hours, including extracting or purifying the nucleic acid taggant from the collected sample. Various embodiments of the invention may utilize a wide range of detection methods besides for PCR and real time PCR, such as DNA microarray, fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection. The method utilized to detect the nucleic acid is dependent on the quantity of nucleic acid taggant associated with the optical reporter marker. When only a few copies of NA taggant are collected in the marker sample, high sensitivity techniques such as PCR may be preferable over fluorescent probes.

Next, the results of the analysis of the collected sample are reviewed and a query or determination is made as to whether or not the specific nucleic acid taggant was detected in the sample. If the DNA taggant is not found or not detected in the collected sample of the item of interest, the conclusion from the analysis is the that item is not a match. If the DNA taggant is detected in the sample, then the item is verified as being authentic and thus a match.

In some embodiments, the quantity or concentration of the nucleic acid taggant within a collected sample can be determined and compared to the initial amount of carrier nucleic acid placed in the item to allow for the detection of fraud caused by diluting the item with inferior products by forgers. In general, such quantitative detection would further comprise, providing an internal or external control to evaluate the efficiency of detection from one sample/analysis to the next. The efficiency of detection may be affected by many parameters such as, probe hybridization conditions, molecules or substances in the good which may interfere with detection, and/or primer integrity, enzyme quality, temperature variations for detection methods utilizing PCR. By providing a control, in the detection methods, any variable conditions can be normalized to obtain an accurate final concentration of the carrier nucleic acid in the item.

In certain embodiments a plurality of DNA taggants with varying sequences associated with a corresponding plurality of optical reporters may be used in labeling a single item. The different nucleic acid tags can be detected qualitatively by the plurality of optical reporters, each with a different emission wavelength linked to a DNA taggant having a uniquely identifiable sequence.

Encapsulation of a Carrier Nucleic Acid

In some embodiments, the carrier nucleic acid is incorporated into the product in the presence of molecules which encapsulate the carrier nucleic acid by forming microspheres. Encapsulating the carrier nucleic acid has the benefit of preventing or at least inhibiting or delaying the degradation of the carrier nucleic acid before recovery for testing or analysis. The materials used in encapsulating can in some embodiments be of plant origin, but can also be synthetically produced materials. The encapsulation of a carrier nucleic acid includes incorporating the carrier nucleic acid into a solvent with a polymer configured to form a microsphere around the carrier nucleic acid which harbors the DNA taggant. The polymers used can be selected from biodegradable or non-biodegradable polymers. Suitable biodegradable polymers are those such as lactic and glycolic acids and esters such as polyanhydrides, polyurethantes, butryic polyacid, valeric polyacid, and the like. Non-biodegradable polymers appropriate for encapsulation are vinyletylenene acetate and acrylic polyacid, polyamides and copolymers as a mixture thereof. The polymers can also be selected from natural compounds such as dextran, cellulose, collagen, albumin, casein and the like.

Certain aspects of the invention comprise labeling the microspheres to benefit in the capture of the nucleic acid tag during the extraction of the label from the product of interest. The microspheres may comprise magnetically charged molecules which allow the microspheres containing the nucleic acid tag to be pulled out of a solution by a magnet.

The microspheres can also be labeled with streptavidin, avidin, biotinylated compounds and the like. Labeling the microspheres aids in the purification of the nucleic acid tag prior to detection and also is useful in concentrating the nucleic acid tag so as to enable in some embodiments, the nucleic acid tag to be detected without PCR amplification.

Carrier Nucleic Acid Extraction and Capture Methods

A variety of nucleic acid extraction solutions have been developed over the years for extracting nucleic acid sequences from a sample of interest. See, for example, Sambrook et al. (Eds.) Molecular Cloning, (1989) Cold Spring Harbor Press. Many such methods typically require one or more steps of, for example, a detergent-mediated step, a protease treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

In some embodiments, the authentication process includes capturing the nucleic acid tag directly with a complementary hybridization probe attached to a solid support. In general, the methods for capturing the nucleic acid tag involve a material in a solid-phase interacting with reagents in the liquid phase. In certain aspects, the nucleic acid probe is attached to the solid phase. The nucleic acid probe can be in the solid phase such as immobilized on a solid support, through any one of a variety of well-known covalent linkages or non-covalent interactions. In certain aspects, the support is comprised of insoluble materials, such as controlled pore glass, a glass plate or slide, polystyrene, acrylamide gel and activated dextran.

In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of capturing the nucleic acid tag, a nucleic acid probe can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin are useful. Examples of other functional group linkers include ester, amide, carbamate, urea, sulfonate, ether, and thioester. A 5' or 3' biotinylated nucleotide can be immobilized on avidin or streptavidin bound to a support such as glass.

Depending on the initial concentration of the nucleic acid tag added to the product of interest, the tag can be detected quantitatively without being amplified by PCR. In some embodiments, a single stranded DNA taggant labeled with a detection molecule (i.e. fluorophore, biotin, etc.) can be hybridized to a complementary probe attached to a solid support to allow for the specific detection of the "detection molecule" configured to the taggant. The DNA taggant can also be double stranded (dsDNA), with at least one strand being labeled with a detection molecule. In the case of a dsDNA taggant, the taggant must be heated sufficiently to melt the double stranded structure and then quick cooled to produce single stranded DNA, where at least one of the strands configured with a detection molecule is capable of hybridizing to the complementary DNA probe under appropriate annealing or hybridization conditions.

In certain aspects of the invention, the complementary probe is labeled with a detection molecule and allowed to hybridize to a strand of the DNA taggant. The hybridization of the probe can be completed within the garment or can be completed after the DNA taggant/carrier nucleic acid containing the DNA taggant has been extracted from the product. The direct detection methods described herein depend on having a large initial concentration of nucleic acid label embedded into the pieces of clothing or rigorous extraction/capture methods which concentrate the nucleic acid tag extracted from a large volume or mass of a particular product.

In one embodiment, wherein the DNA taggant includes an up converting phosphor (UCP) particle, the extraction of the DNA taggant varies depending on the garment being authenticated. When the carrier nucleic acid and DNA taggant are linked to one or more UCP particles, the carrier nucleic acid and DNA taggant can be located by detecting the presence of the UCP by an appropriate light source. The DNA taggant can then be extracted from the item by scraping, cutting out, or dissolving the portion of the garment which is determined to have the presence of the correct up-converting phosphor particle(s). Once the portion of the item containing the DNA taggant has been removed from the item of interest, the DNA taggant may isolated and/or amplified by PCR using techniques known to those skilled in the art.

Real-Time PCR Amplification

In many embodiments, the authentication process comprises amplifying the nucleic tag by polymerase chain reaction. However, conventional PCR amplification is not a quantitative detection method. During amplification, primer dimers and other extraneous nucleic acids are amplified together with the nucleic acid corresponding to the analyte. These impurities must be separated, usually with gel separation techniques, from the amplified product resulting in possible losses of material. Although methods are known in which the PCR product is measured in the log phase, these methods require that each sample have equal input amounts of nucleic acid and that each sample amplifies with identical efficiency, and are therefore, not suitable for routine sample analyses. To allow an amount of PCR product to form which is sufficient for later analysis and to avoid the difficulties noted above, quantitative competitive PCR amplification uses an internal control competitor and is stopped only after the log phase of product formation has been completed.

In a further development of PCR technology, real time quantitative PCR has been applied to nucleic acid analytes or templates. In this method, PCR is used to amplify DNA in a sample in the presence of a non-extendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time. Reverse transcriptase (RT)-real time PCR (RT-PCR) has also been described (Gibson et al., 1996). Numerous commercially thermal cyclers are available that can monitor fluorescent spectra of multiple samples continuously in the PCR reaction, therefore the accumulation of PCR product can be monitored in 'real time' without the risk of amplicon contamination of the laboratory. Heid, C. A.; Stevens, J.; Livak, K. L.; Williams, P. W. (1996). Real time quantitative PCR. Gen. Meth. 6: 986-994.

In some embodiments of the anti-counterfeit authentication process, real time PCR detection strategies may be used, including known techniques such as intercalating dyes (e.g. ethidium bromide) and other double stranded DNA binding dyes used for detection (such as SYBR green, a highly sensitive fluorescent stain obtainable from FMC Bioproducts), dual fluorescent probes (Wittwer, C. et al., (1997) Bio-Techniques 22: 176-181) and panhandle fluorescent probes (i.e. molecular beacons; Tyagi S., and Kramer FR. (1996) Nature Biotechnology 14: 303-308). Although intercalating dyes and double stranded DNA binding dyes permit quantitation of PCR product accumulation in real time applications, they suffer from the previously mentioned lack of specificity, detecting primer dimer and any non-specific amplification product. Careful sample preparation and handling, as well as careful primer design, using known techniques must be practiced to minimize the presence of matrix and contaminant DNA and to prevent primer dimer formation. Appropriate PCR instrument analysis software and melting temperature analysis permit a means to extract specificity and may be used with these embodiments.

PCR amplification is performed in the presence of a non-primer detectable probe which specifically binds the PCR amplification product, i.e., the amplified detector DNA moiety. PCR primers are designed according to known criteria and PCR may be conducted in commercially available instruments. The probe is preferably a DNA oligonucleotide specifically designed to bind to the amplified detector molecule. The probe preferably has a 5' reporter dye and a downstream 3' quencher dye covalently bonded to the probe, which allows fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan® PCR system from Perkin-Elmer, which allows real time PCR detection.

In an alternative embodiment, the reporter dye and quencher dye may be located on two separate probes which hybridize to the amplified PCR detector molecule in adjacent locations sufficiently close to allow the quencher dye to quench the fluorescence signal of the reporter dye. As with the detection system described above, the 5'-3' nuclease activity of the polymerase cleaves the one dye from the probe containing it, separating the reporter dye from the quencher dye located on the adjacent probe preventing quenching of the reporter dye. As in the embodiment described above, detection of the PCR product is by measurement of the increase in fluorescence of the reporter dye.

Molecular beacons systems are frequently used with real time PCR for specifically detecting the nucleic acid template in the sample quantitatively. For instance, the Roche Light Cycler™ or other such instruments may be used for this purpose. The detection molecule configured to the molecular beacon probe may be visible under daylight or conventional lighting and/or may be fluorescent. It should also be noted that the detection molecule may be an emitter of radiation, such as a characteristic isotope.

The ability to rapidly and accurately detect and quantify biologically relevant molecules with high sensitivity is a central issue for medical technology, national security, public safety, and civilian and military medical diagnostics. Many of the currently used approaches, including enzyme linked immunosorbent assays (ELISAs) and PCR are highly sensitive. However, the need for PCR amplification makes a detection method more complex, costly and time-consuming. In certain embodiments anti-counterfeit nucleic acid tags are detected by Surface Enhanced Raman Scattering (SERS) as described in U.S. Pat. No. 6,127,120 by Graham et al. SERS is a detection method which is sensitive to relatively low target (nucleic acid) concentrations, which can preferably be carried out directly on an unamplified samples. Nucleic acid tags and/or nucleic acid probes can be labeled or modified to achieve changes in SERS of the nucleic acid tag when the probe is hybridized to the nucleic acid tag. The use of SERS for quantitatively detecting a nucleic acid provides a relatively fast method of analyzing and authenticating a particular product.

Another detection method useful in the invention is the Quencher-Tether-Ligand (QTL) system for a fluorescent biosensor described in U.S. Pat. No. 6,743,640 by Whitten et al. The QTL system provides a simple, rapid and highly-sensitive detection of biological molecules with structural specificity. QTL system provides a chemical moiety formed of a quencher (Q), a tethering element (T), and a ligand (L). The system is able to detect target biological agents in a sample by observing fluorescent changes.

The QTL system can rapidly and accurately detect and quantify target biological molecules in a sample. Suitable examples of ligands that can be used in the polymer-QTL approach include chemical ligands, hormones, antibodies, antibody fragments, oligonucleotides, antigens, polypeptides, glycolipids, proteins, protein fragments, enzymes, peptide nucleic acids and polysaccharides. Examples of quenchers for use in the QTL molecule include methyl viologen, quinones, metal complexes, fluorescent dyes, and electron accepting, electron donating and energy accepting moieties. The tethering element can be, for example, a single bond, a single divalent atom, a divalent chemical moiety, and a multivalent chemical moiety. However, these examples of the ligands, tethering elements, and quenchers that form the QTL molecule are not to be construed as limiting, as other suitable examples would be easily determined by one of skill in the art.

Kits for Authenticating Items Using Nucleic Acid-Linked Optical Reporters

The invention also provides kits for authenticating items of interest using the methods of the invention. The kits of the invention may include, for example, a container enclosing the optical reporter marker, and a sample tube for holding a collected sample of the item or item to be authenticated. The kits may also include an applicator for sampling an item. The kits may still further include a collection tool for taking a sample of the labeled item for transfer to the sample tube. The kits may yet further include a suitable portable light source for detecting the optical reporters.

By way of example, the optical reporter marker may be in the form of a liquid solution or dispersion, and the container with the kit would be suitably configured for holding a liquid. The applicator of the kit may comprise an "eye-dropper" for applying liquid optical reporter marker solution to the item in droplet form, a spatula for smearing the solution on an item, a syringe for injecting the solution into an item, or like type of applicator. The collection tool of the kit may comprise a spoon, gouge, a scraping or abrading tool for removing a sample of the labeled item, a blade or scissors for cutting a piece of the item, a cloth (which may be solvent-moistened) for wiping a sample from the item, or the like. The sample tube of the kit may comprise a sealable vial or eppendorf tube, and may contain solvent or solution for extraction of the optical reporter marker from the sample taken from the tagged item. The portable light source of the kit may comprise a hand-held UV lamp suitable for detecting the optical reporter marker.

The kit may further include one or more primers and/or probes as well as solutions appropriate for PCR analysis. The kit may further include a PCR instrument for analysis of the extracted optical reporter marker. The kits of the invention thus provide a convenient, portable system for practicing the methods of the invention.

Synthesis of UCP Particles Covalently Linked to Biomolecules

Nucleotide-labeled optical reporters in accordance with the invention can be made by a variety of methods, including those depicted in the co-pending U.S. application "Methods for linking Optical Reporters to Biomolecules," which is hereby incorporated by reference.

In addition, other optical reporters such as, for example, ultraviolet (UV) reporters, Up Converting Phosphor (UCP) infrared (IR), red UV marker, UV fluorophore, ceramic IR marker, protein taggants, and/or trace element reporters can be used in combination with the carrier nucleic acid that incorporates the DNA taggant(s). In an exemplary embodiment, the taggants used can include, for example, a combination of DNA taggants, and an infrared upconverting phosphor (UCP) reporter. Alternatively, in another exemplary embodiment, the taggants used can include, for example, a combination of DNA taggants, an infrared upconverting phosphor (UCP) reporter and a UV reporter. For example, in an exemplary embodiment, the (UCP) IR reporter can be, for example, a green, a blue or a red (UCP) IR reporter, such as for instance the Green IR Marker, Product No. BPP-1069; the Blue UCP, Product No. BPP-1070; or the Red UCP, Product No. BPP-1071 from Boston Applied Technologies Inc., Woburn, Mass.

The objects of interest marked with carrier nucleic acid that incorporates the DNA taggants according to exemplary embodiments of the present invention include, for example, ceramic surfaces, plastic films, vinyl sheets, antiques, items of jewelry, identification cards, credit cards, magnetic strip cards, paintings, artwork, souvenirs, sports collectibles and other collectibles. The authenticity of these objects can then be verified by recovering and identifying the taggants coated thereon through, for example, methods described in further detail below.

In another embodiment, the taggant includes an infrared upconverting phosphor (UCP) taggant and a DNA taggant. In exemplary embodiments of the present invention, the taggant can be recovered from the taggant-coated portion of the object without disturbing the appearance of the object. In anther embodiment, the unique taggant is a DNA taggant having a unique DNA sequence and the unique non-natural DNA sequence is stored in a database that matches the unique DNA sequence to the data elements corresponding to the object which is coated with the unique taggant. The database can in turn be located on a computer that can be accessed in order to locate, track, authenticate and verify the identity of the tagged object from which the taggant was recovered.

DNA taggants useful in the examples described below include any suitable DNA taggant, such as for instance, in one embodiment, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs. Alternatively, the DNA taggant can be single-stranded DNA of any suitable length, such as between about 40 bases and about 1000 bases; between about 80 and 500 bases; or between about 100 and about 250 bases. The DNA taggant can be natural DNA, whether isolated from natural sources or synthetic; or the DNA taggant can be a synthetically produced non-natural sequence. All or a portion of the DNA may comprise an identifiable sequence.

In one exemplary embodiment, the DNA taggant is identifiable by any suitable detection and/or identification method such as for example, hybridization with a taggant-sequence specific nucleic acid probe, an in situ hybridization method (including fluorescence in situ hybridization: FISH), amplification using a polymerase chain reaction (PCR), such as quantitative/real time PCR and detection of the amplified sequences (amplicons) by any of the variety of standard well known methods.

For example, in the PCR identification method, the nucleic acid taggants, e.g., DNA taggants recovered from the object are amplified by polymerase chain reaction (PCR) and resolved by gel electrophoresis. Since the sequence of the nucleic acid taggants of the present invention are unique and specific to the tagged object, the original nucleic acid will be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant. In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence of the from the authentic object. Furthermore, the random amplicons derived from counterfeit articles are also of random lengths and the likelihood of producing amplicons of the exact lengths specified by the taggant-specific primers is vanishingly small. Therefore, by comparing the sizes and amount of PCR products, the authenticity of labeled objects can be verified, non-authentic objects can be screened and rejected and anti-counterfeit screening purpose is then achieved.

The number of amplicons amplified and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels and the electrophoretic separation can be in any suitable format, such as for instance in a slab gel or by capillary electrophoresis.

EXAMPLES

It should be understood that the following examples set forth are intended to be illustrative only and that exemplary embodiments of the present invention are not limited to the conditions or materials recited therein.

The following examples illustrate embodiments of the present invention to mark an inventory item with a marker smoke including a carrier nucleic acid that includes a DNA taggant having a uniquely identifiable sequence.

Example 1

Detection of DNA Taggant on Fabrics after Exposure to Marker Smoke

Fifty microliters of carrier nucleic acid (40 mg/mL in deionized water) containing the double stranded 199 base pair DNA taggant at a concentration of 0.5 mg/L was activated by mixing with 50 uL 0.6 M NaOH solution (EMD Millipore Chemicals, ACS grade) in a disposable snap cap microtube and allowed to stand at room temperature for 30 minutes. The activated nucleic acid mixture was then transferred to a 15 mL conical plastic test tube (BD Falcon Labware) and 9.9 mL poly-L-lysine (0.1% w/v, Sigma-Aldrich) was added and thoroughly mixed. This solution was then added to 990 mL SmokeCloak FL600V smoke fluid to provide the marker smoke fluid used in the examples described below. The marker smoke fluid was transferred to the reservoir of a SmokeCloak fog machine (Val V10) obtained from SmokeCloak, Odense, Denmark.

In an empty room measuring eight feet by ten feet and having a nine foot ceiling, several pieces of test fabrics of cotton and wool and clothing articles were placed on the floor, suspended from the ceiling, and attached to the wall at different heights.

The SmokeCloak fog machine loaded with the marker smoke fluid was placed on the floor adjacent to the open entrance door and turned-on to discharge fog into the room. The door was closed and the smoke was allowed to dissipate for about 5 minutes by which time the marker smoke thinned out sufficiently for the operator to see the location of the test fabrics. No visible change to the fabrics or clothing after exposure to the marker smoke was evident. These fabrics and items of clothing were then collected by the operator and taken to the laboratory for analysis. The collected fabric samples and articles of clothing retrieved from different locations of the room were labeled and stored in sealed plastic bags. All samples were sent to the lab and were forensically authenticated.

PCR analysis of samples was performed using a primer pair complementary to the uniquely identifiable sequence of the DNA taggant concealed within the carrier nucleic acid present in the marker smoke.

FIG. 1 shows representative scans obtained by capillary electrophoresis of PCR products from samples taken from a cotton fabric and a woolen fabric retrieved from the room after exposure to the marker smoke.

Example 2

Detection of DNA Taggant on Operator Immediately after Exposure

Samples from the operator were also collected. Medical tape, skin, coat, and shoes were stripped by attaching and removing medical tape and the pieces of tape were sent to the lab for analysis. The operator's hair and nostrils were swabbed using generic cotton swabs and the swabs submitted for PCR analysis.

Figure 2:
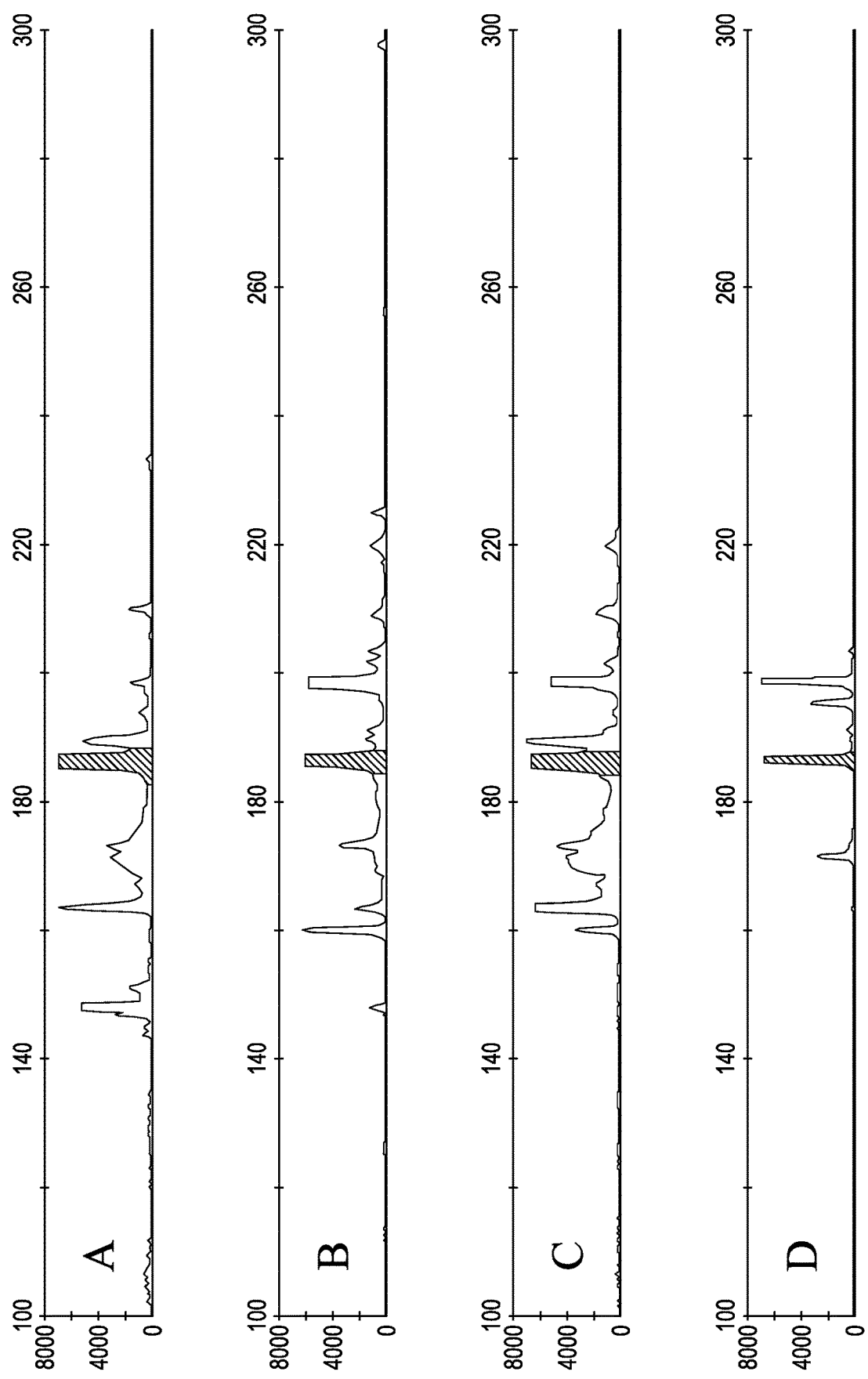
FIG. 2 shows DNA authentication from an operator immediately after exposure to marker smoke that includes a carrier nucleic acid and a DNA taggant having a uniquely identifiable sequence. The panels A, B, C and D show traces of PCR amplification products from samples taken from swabs of the operator's nostril, skin, jacket and shoes respectively after separation by capillary electrophoresis.
Figure 3:
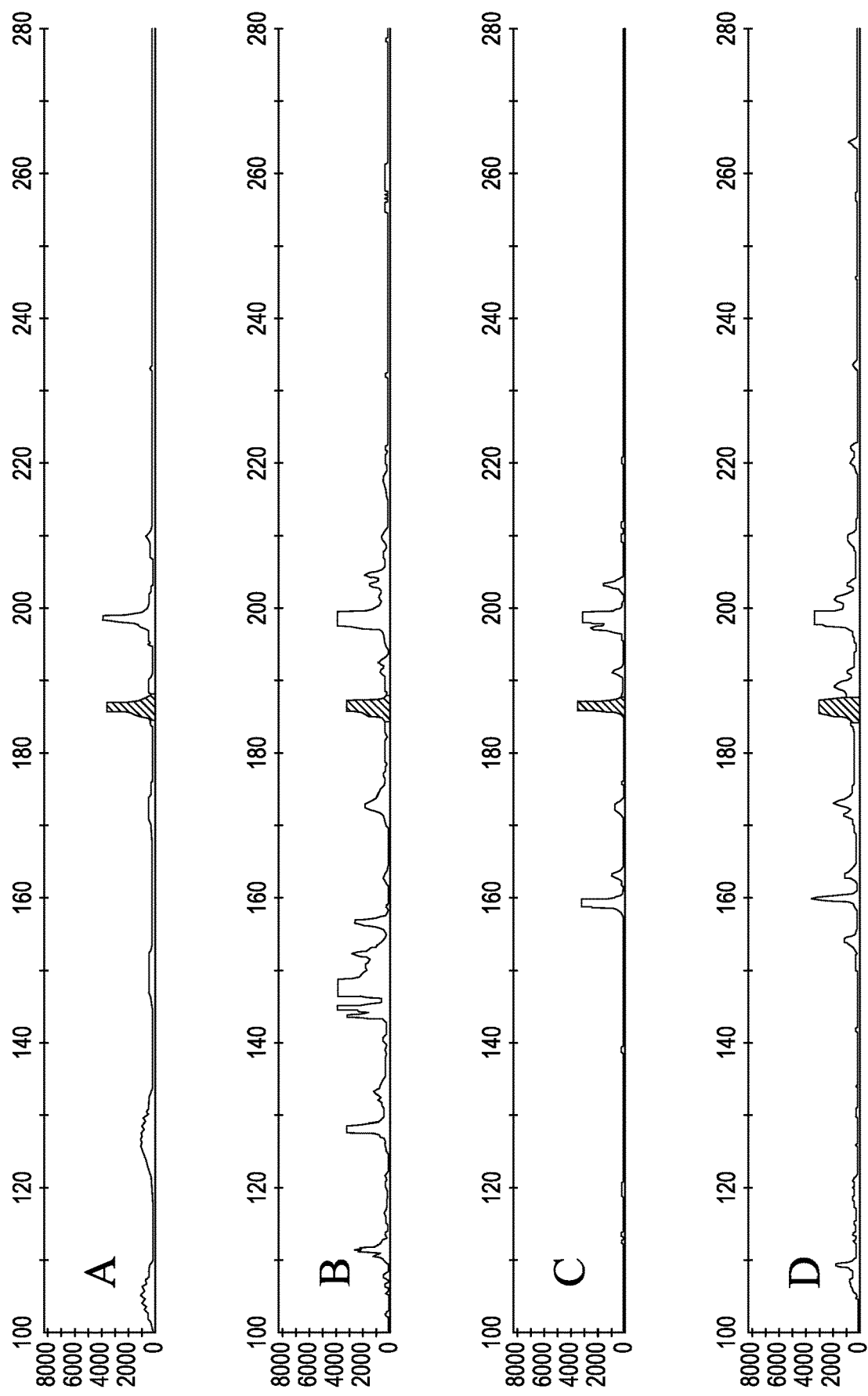
FIG. 3 shows DNA authentication from an operator after 48 hours post exposure to marker smoke that includes a carrier nucleic acid and a DNA taggant having a uniquely identifiable sequence. The four panels A, B, C and D show traces from capillary electrophoresis separation of PCR amplification products from samples taken from swabs of the operator's nostril, skin, jacket and shoes, respectively.

FIG. 2 shows capillary electrophoresis scans of PCR products from samples taken from the operator. Panels show PCR products from sample from the operator immediately after retrieving the fabric and clothing items as described in Example 1. (A) Nasal swab; (B) Swab of exposed skin; (C) Tape after sampling operator's jacket; (D) Tape after sampling operator's shoes.

Example 3

Detection of DNA Taggant on Operator 48 Hours Post-Exposure

Forty-eight hours later, after the operator had taken at least two showers additional samples were taken from the operator. All samples were sent to the lab and were forensically authenticated by PCR and capillary electrophoresis for the presence of DNA taggant as described above. Panels show PCR products from sample from the operator (A) Hair sample; (B) Nasal swab; (C) Swab of exposed skin; (D) Tape after sampling operator's shoes.

Example 4

Detection of DNA Taggant on Operator One Week Post-Exposure

Figure 4:
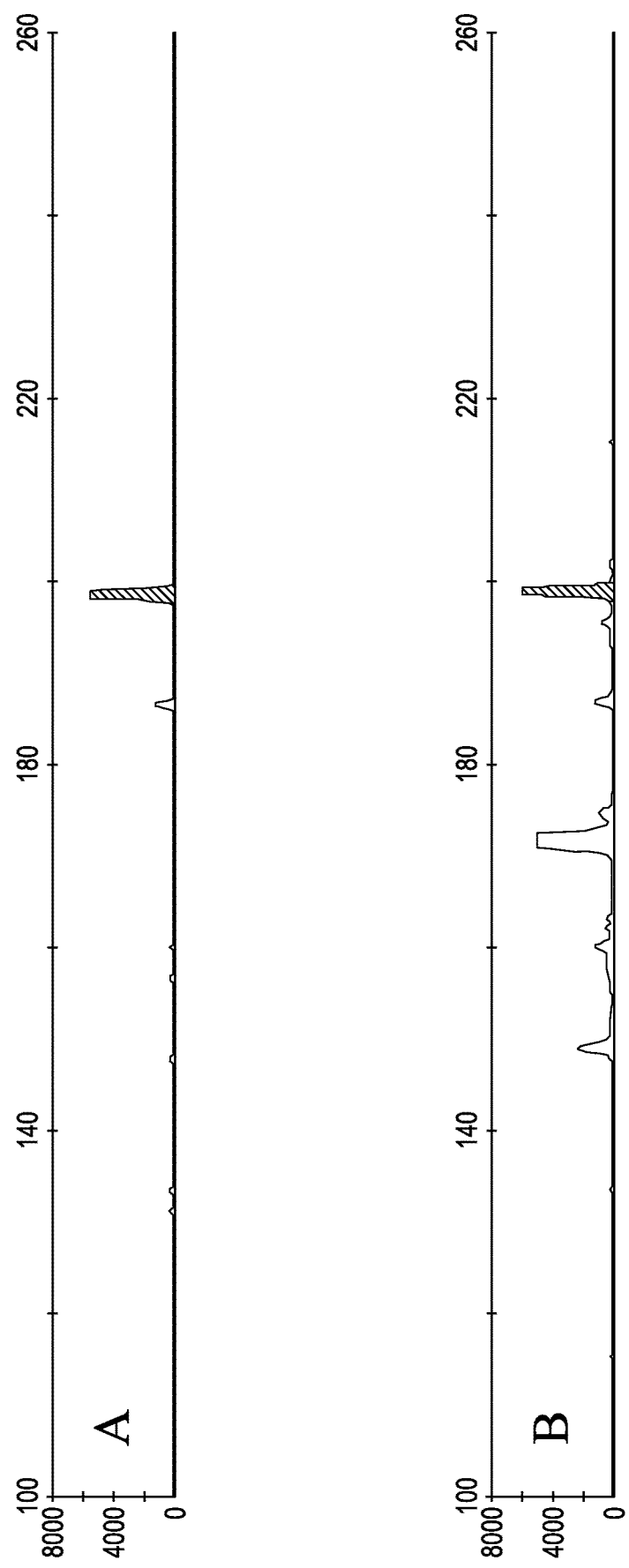
FIG. 4 shows DNA authentication from hands and shoes of an operator up to one week post exposure to marker smoke that includes a carrier nucleic acid and a DNA taggant having a uniquely identifiable sequence. Panel A shows a trace from a capillary electrophoresis separation of PCR amplification products from a sample obtained by swabbing the operator's hand six days after exposure. Panel B shows a trace from a capillary electrophoresis separation of PCR amplification products from a sample obtained by swabbing the operator's shoes one week after exposure to marker smoke that includes a carrier nucleic acid with a DNA taggant having a uniquely identifiable sequence.
Figure 5:
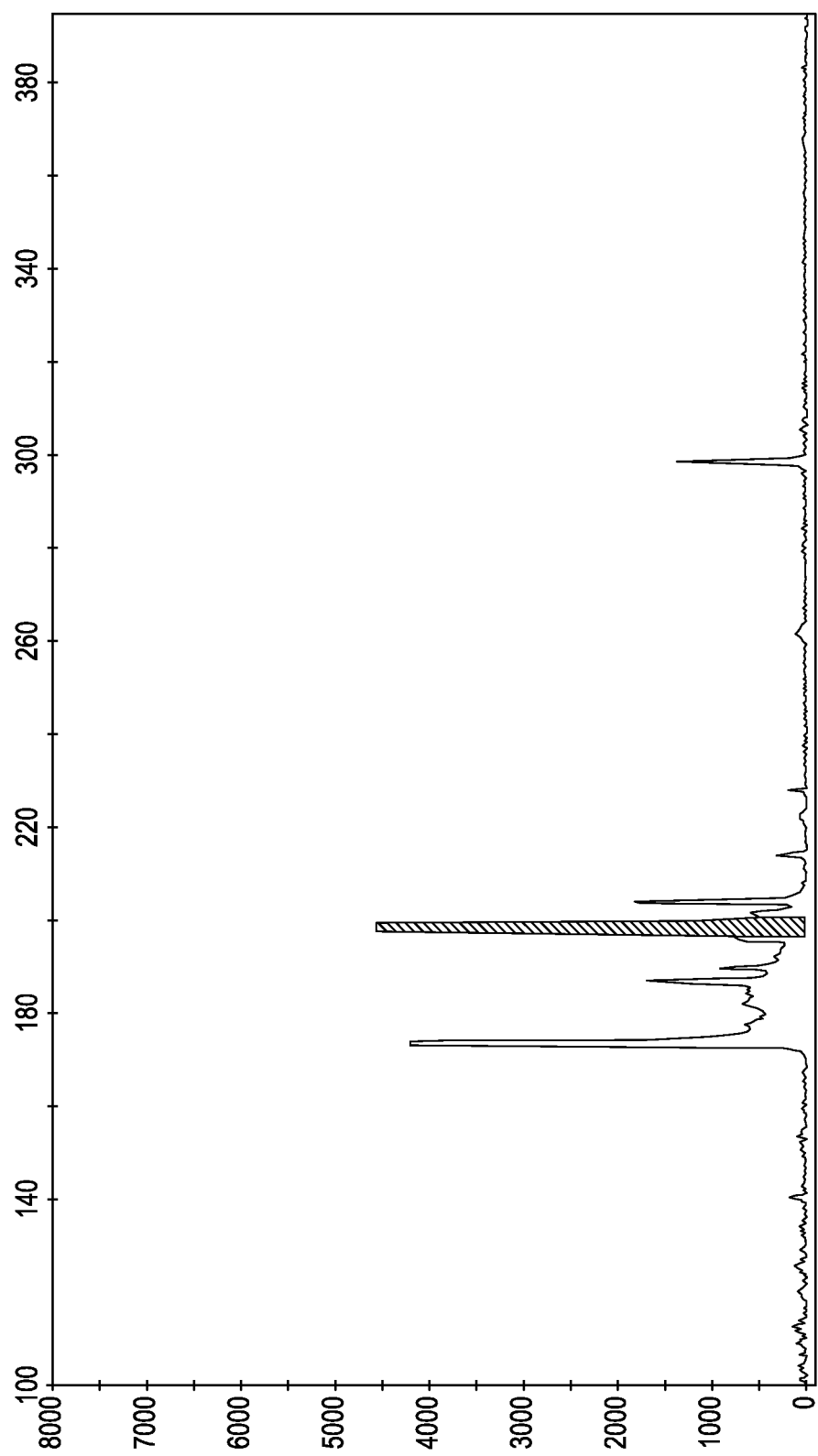
FIG. 5 shows authentication of a wool jacket thirty days after exposure to marker smoke that includes a carrier nucleic acid and a DNA taggant having a uniquely identifiable sequence, the jacket having been subjected to dry cleaning after exposure to marker smoke that includes a carrier nucleic acid with a DNA taggant having a uniquely identifiable sequence.

Six and seven days after the marker smoke experiment and after the operator had taken normal showers, additional samples were taken from the operator and analyzed again for the presence of DNA taggant. Unmistakable DNA taggant amplicon was detected in all samples including skin and shoes, as shown in FIG. 4, panels (A) and (B) respectively.

Example 5

Authentication of Wool Jacket after Dry Cleaning 30 days post experiment and after dry cleaning of operator's jacket, a sample was taken from the jacket and DNA was analyzed as described above. Again, a Unmistakable DNA taggant amplicon was detected, demonstrating that DNA taggant survived the dry cleaning and the week of normal wear. Thus DNA taggant adducted to these various substrates robustly and resiliently as was demonstrated by DNA taggant detection even after several washes and a week of normal use.

Having described exemplary embodiments of the present invention, it will be readily apparent to those of reasonable skill in the art that various modifications may be made without departing from the spirit and scope of the invention which is defined by the metes and bounds of the appended claims.

What is claimed is:

1. A method of marking an inventory item consisting of: providing a water-based fog generator, providing a reservoir for holding a marker fluid and adapted to provide the flow of marker fluid to the fog generator; the reservoir containing marker fluid consisting of i) a double-stranded carrier nucleic acid; ii) a double-stranded DNA taggant having a uniquely identifiable sequence, wherein said double-stranded DNA taggant is unencapsulated; and iii) deionized water;
activating the water-based fog generator to produce a non-electrostatically charged marker fluid fog so as to cause the marker fluid fog to flow over the inventory item and thereby to detectably mark the inventory item with the unencapsulated double-stranded DNA taggant, wherein the unencapsulated double-stranded DNA taggant is less than one part per then thousand by weight of the double-stranded carrier DNA and is detected by real-time PCR.

2. The method of claim 1, wherein uniquely identifiable sequence of the unencapsulated double-stranded DNA taggant is a sequence of from about 25 bases to about 10,000 bases in length.

3. The method of claim 2, wherein the uniquely identifiable sequence of the unencapsulated double-stranded DNA taggant is a sequence of from about 50 bases to about 5,000 bases in length.

4. The method of claim 3, wherein the uniquely identifiable sequence of the unencapsulated double-stranded DNA taggant is a sequence of from about 75 bases to about 500 bases in length.

5. The method of claim 1, wherein the unencapsulated double-stranded DNA taggant having a uniquely identifiable sequence is less than one part per hundred thousand by weight of the carrier nucleic acid.

6. The method of claim 5, wherein the unencapsulated double-stranded DNA taggant having a uniquely identifiable sequence is less than one part per million by weight of the carrier nucleic acid.

7. The method of claim 1, further comprising detecting the unencapsulated double-stranded DNA taggant of the detectably marked inventory item and thereby authenticating the detectably marked inventory item.

8. The method of claim 7, wherein the detection of the unencapsulated double-stranded DNA taggant comprises a PCR amplification step.

* * * * *